US008541218B2

(12) United States Patent
Barany et al.

(10) Patent No.: US 8,541,218 B2
(45) Date of Patent: *Sep. 24, 2013

(54) HIGH FIDELITY THERMOSTABLE LIGASE AND USES THEREOF

(75) Inventors: Francis Barany, New York, NY (US); Weiguo Cao, New York, NY (US); Jie Tong, Forest Hills, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 804 days.

This patent is subject to a terminal disclaimer.

(21) Appl. No.: 11/167,048

(22) Filed: Jun. 24, 2005

(65) Prior Publication Data
US 2005/0266487 A1 Dec. 1, 2005

Related U.S. Application Data

(63) Continuation of application No. 09/830,502, filed as application No. PCT/US99/25437 on Oct. 29, 1999, now Pat. No. 6,949,370.

(60) Provisional application No. 60/106,461, filed on Oct. 30, 1998.

(51) Int. Cl.
*C12N 9/00* (2006.01)
*C12N 15/52* (2006.01)

(52) U.S. Cl.
USPC .......................... 435/183; 435/193; 530/350

(58) Field of Classification Search
None
See application file for complete search history.

(56) References Cited

U.S. PATENT DOCUMENTS

| | | | |
|---|---|---|---|
| 4,683,202 A | 7/1987 | Mullis | |
| 4,883,750 A | 11/1989 | Whiteley et al. | |
| 5,470,705 A | 11/1995 | Grossman et al. | |
| 5,494,810 A | 2/1996 | Barany et al. | |
| 5,496,699 A | 3/1996 | Sorenson | |
| 5,506,137 A | 4/1996 | Mathur et al. | |
| 5,516,663 A | 5/1996 | Backman et al. | |
| 5,728,526 A | 3/1998 | George, Jr. et al. | |
| 5,912,148 A | 6/1999 | Eggerding | |
| 6,054,564 A | 4/2000 | Barany et al. | |
| 6,312,892 B1 | 11/2001 | Barany et al. | |
| 6,576,453 B2 | 6/2003 | Barany et al. | |

FOREIGN PATENT DOCUMENTS

| | | |
|---|---|---|
| WO | WO 91/17239 | 11/1991 |
| WO | WO 93/17126 | 9/1993 |
| WO | WO 97/31256 | 8/1997 |
| WO | WO 97/45559 | 12/1997 |
| WO | WO 98/03673 | 1/1998 |
| WO | WO 00/26381 | 5/2000 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*

Kreiner, T., "Rapid Genetic Sequence Analysis Using a DNA Probe Array System," *American Laboratory* 39-43 (Mar. 1996).
Kovach et al., "Mutation Detection by Highly Sensitive Methods Indicates That p53Gene Mutations in Breast Cancer Can Have Important Prognostic Value," *Proc. Natl Acad. Sci. USA* 93:1093-96 (1996).
Lin et al., "Multiplex Genotype Determination at a Large Number of Gene Loci," *Proc. Natl. Acad. Sci. USA* 93:2582-87 (1996).
Tavormina et al., "Thanatophoric Dysplasia (Types I and II) Caused by Distinct Mutations in Fibroblast Growth Factor Receptor 3," *Nature Genetics* 9:321-328 (1995).
Barany et al., "Cloning, Overexpression and Nucleotide Sequence of a Thermostable DNA Ligase-Encoding Gene," *Gene* 109:1-11 (1991).
Sidransky et al., "Identification of *ras* Oncogene Mutations in the Stool of Patients With Curable Colorector Tumors," *Science* 256:102-105 (1992).
Brennan et al., "Molecular Assessment of Histopathological Staging in Squamous-Cell Carcinoma of the Head and Neck," *The New England Journal of Medicine* 332(7):429-35 (1995).
Berthélemy et al., "Identification of K-*ras* Mutations in Pancreatic Juice in the Early Diagnosis of Pancreatic Cancer," *Annals of Internal Medicine* 123(3):188-91 (1995).
Hayashi et al., "Genetic Diagnosis Identifies Occult Lymph Node Metastases Undetectable by the Histopathological Method," *Cancer Research* 54:3853-56 (1994).
Tada et al., "Detection of *ras* Gene Mutations in Pancreatic Juice and Peripheral Blood of Patients with Pancreatic Adenocarcinoma," *Cancer Research* 53:2472-74 (1993).
Tada et al., "Clinical Application of *ras* Gene Mutation for Diagnosis of Pancreatic Adenocarcinoma," *Gastroenterology* 100:233-38 (1991).
Mitsudomi et al., "Mutations of *ras* Genes Distinguish a Subset of Non-Small-Cell Lung Cancer Cell Lines From Small-Cell Lung Cancer Cell Lines," *Oncogene* 6:1353-62 (1991).
Day et al., "Detection of Steroid 21-Hydroxylase Alleles Using Gene-Specific PCR and a Multiplexed Ligation Detection Reaction," *Genomics* 29:152-62 (1995).
Frenkel et al., "Specific, Sensitive, and Rapid Assay for Human Immunodeficiency Virus Type 1 *pol* Mutations Associated With Resistance to Zidovudine and Didanosine," *J. Clin. Microbiol.* 33(2):342-47 (1995).
Abravaya et al., "Detection of Point Mutations With a Modified Ligase Chain Reaction (Gap-LCR)," *Nucleic Acids Research* 23(4):675-82 (1995).
Powell et al., "Molecular Diagnosis of Familial Adenomatous Polyposis," *The New England Journal of Medicine* 329(27):1982-87 (1993).

(Continued)

Primary Examiner — Richard Hutson
(74) Attorney, Agent, or Firm — LeClairRyan, a Professional Corporation

(57) ABSTRACT

The present invention is directed to a mutant thermostable ligase having substantially higher fidelity than either T4 ligase or *Thermus thermophilus* ligase. The ligase of the present invention is a mutant of a wild-type thermostable ligase having a histidine adjacent a KXDG motif, where the mutant thermostable ligase has a mutation in its amino sequence where the histidine adjacent the KXDG motif in the wild-type thermostable ligase is replaced with an arginine, and wherein X is any amino acid. The DNA molecule encoding this enzyme as well as expression systems and host cells containing it are also disclosed. The thermostable ligase of the present invention is useful in carrying out a ligase detection reaction process and a ligase chain reaction process.

1 Claim, 7 Drawing Sheets

(56) References Cited

OTHER PUBLICATIONS

Jen et al., "Molecular Determinants of Dysplasia in Colorectal Lesions," *Cancer Research* 54:5523-26 (1994).
Redston et al., "Common Occurrence of APC and K-*ras* Gene Mutations in the Spectrum of Colitis-Associated Neoplasias," *Gastroenterology* 108:383-92 (1995).
Lu et al., "Quantitative Aspects of the Mutant Analysis by PCR and Restriction Enzyme Cleavage (MAPREC)," *PCR Methods and Applications* 3:176-80 (1993).
Kuppuswamy et al., "Single Nucleotide Primer Extension to Detect Genetic Diseases: Experimental Application to Hemophilia B (factor IX) and Cystic Fibrosis Genes," *Proc. Natl. Acad. Sci. USA* 88:1143-47 (1991).
Rust et al., "Mutagenically Separated PCR (MS-PCR): A Highly Specific One Step Procedure for Easy Mutation Detection," *Nucleic Acid Research* 21(16):3623-29 (1993).
Suzuki et al., "Detection of *ras* Gene Mutations in Human Lung Cancers by Single-Strand Conformation Polymorphism Analysis of Polymerase Chain Reaction Products," *Oncogene* 5:1037-43 (1990).
Balles et al., "Facilitated Isolation of Rare Recombinants by Ligase Chain Reaction: Selection for Intragenic Crossover Events in the *Drosophila* optomotor-blind Gene," *Mol. Gen. Genet.* 245:734-40 (1994).
Reynolds et al., "Analysis of Genetic Markers in Forensic DNA Samples Using the Polymerase Chain Reaction," *Anal. Chem.* 63:2-15 (1991).
Buyse et al., "Rapid DNA Typing of Class II HLA Antigens Using the Polymerase Chain Reaction and Reverse Dot Blot Hybridization," *Tissue Antigens* 41:1-14 (1993).
Gyllensten et al., "PCR-Based HLA Class II Typing," *PCR Meth. Appl.* 1:91-98 (1991).
Chamberlain et al., "Deletion Screening of the Duchenne Muscular Dystrophy Locus Via Multiplex DNA Amplification," *Nucleic Acids Res.* 16:11141-56 (1988).
Tsui, L. C., "Mutations and Sequence Variations Detected in the Cystic Fibrosis Transmembrane Conductance Regulator (CFTR) Gene: A Report From the Cystic Fibrosis Genetic Analysis Consortium," *Human Mutat.* 1:197-203 (1992).
Hollstein et al., "p53 Mutations in Human Cancers," *Science* 253:49-53 (1991).
Saiki et al., "Enzymatic Amplification of β-Globin Genomic Sequences and Restriction Site Analysis for Diagnosis of Sickle Cell Anemia," *Science* 230:1350-1354 (1985).
Wu et al., "The Ligation Amplification Reaction (LAR)—Amplification of Specific DNA Sequences Using Sequential Rounds of Template-Dependent Ligation," *Genomics* 4:560-569 (1989).
Landegren et al., "A Ligase-Mediated Gene Detection Technique," *Science* 241:1077-80 (1988).
Winn-Deen, et al., "Sensitive Fluorescence Method for Detecting DNA Ligation Amplification Products," *Clinical Chemistry* 37(9):1522-23 (1991).
Barany, F., "Genetic Disease Detection and DNA Amplification Using Cloned Thermostable Ligase," *Proc. Nat'l Acad. Sci. USA* 88:189-93 (1991).
Grossman et al., "High-Density Multiplex Detection of Nucleic Acid Sequences: Oligonucleotide Ligation Assay and Sequence-Coded Separation," *Nucl. Acids Res.* 22(21):4527-34 (1994).
Jou et al., "Deletion Detection in the Dystrophin Gene by Multiplex Gap Ligase Chain Reaction and Immunochromatographic Strip Technology," *Human Mutation* 5:86-93 (1995).
Gibbs et al., "Detection of Single DNA Base Differences by Competitive Oligonucleotide Priming," *Nucleic Acids Res.* 17:2437-48 (1989).
Chehab et al., "Detection of Specific DNA Sequences by Fluorescence Amplification: A Color Complementation Assay," *Proc. Natl. Acad. Sci. USA* 86:9178-82 (1989).
Livak et al., "Detection of Single Base Differences Using Biotinylated Nucleotides With Very Long Linker Arms," *Nucleic Acids Res.* 20(18):4831-37 (1992).
Nickerson et al., "Automated DNA Diagnostics Using an ELISA-Based Oligonucleotide Ligation Assay," *Proc. Natl. Acad. Sci. USA* 87:8923-27 (1990).
Dong et al., "Mutational Studies of Human DNA Polymerase α," *J. Biol. Chem.* 268(32):24175-24182 (1993).
Copeland et al., "Fidelity Studies of the Human DNA Polymerase α," *J. Biol. Chem.* 268(15):11041-11049 (1993).
Reha-Krantz et al., "Motif A of Bacteriophage T4 DNA Polymerase: Role in Primer Extension and DNA Replication Fidelity," *J. Biol. Chem.* 269(8):5635-5643 (1994).
Eggerding, F., "A One-Step Coupled Amplification and Oligonucleotide Ligation Procedure for Multiplex Genetic Typing," *PCR Methods and Applications* 4:337-345 (1995).
Friedhoff et al., "Quantitative Polymerase Chain Reaction with Oligodeoxynucleotide Ligation Assay/Enzyme-Linked Immunosorbent Assay Detection," *Anal. Biochem.* 215:9-16 (1993).
Wallace et al., "Ligase Chain Reaction for the Detection of Specific DNA Sequences and Point Mutations," in Pfeifer, ed., Technologies for Detection of DNA Damage and Mutations at 307-322, Plenum Press, New York, NY (1996).
Reyes et al., "Ligase Chain Reaction Assay for Human Mutations: The Sickle Cell by LCR Assay," *Clinical Chemistry* 43(1):40-44 (1997).
Jónsson et al., "Sequence of the DNA Ligase-Encoding Gene from *Thermus scotoductus* and Conserved Motifs in DNA Ligases," *Gene* 151:177-180 (1994).
Luo et al., "Improving the Fidelity of *Thermus thermophilus* DNA Ligase," *Nucleic Acids Res.* 24:3071-3078 (1996).
Luo et al., "Identification of Essential Residues in *Thermus thermophilus* DNA Ligase," *Nucleic Acids Res.* 24:3079-3085 (1996).
Tong et al., "Biochemical Properties of a High Fidelity DNA Ligase from *Thermus* Species AK16D," *Nucleic Acids Research* 27:788-794 (1999).
Zirvi et al., "Ligase-Based Detection of Mononucleotide Repeat Sequences," *Nucleic Acids Research* 27(24):e40i-e40viii (1999).
Ngo et al., "Computational Complexity, Protein Structure Prediction, and the Levinthal Paradox," in *The Protein Folding Problem and Tertiary Structure Prediction*, Merz et al., Eds., Boston, MA: Birkhauser, Chapter 14, pp. 433 and 491-495 (1994).
Takahashi et al., "Purification of HB8 DNA Ligase by Red Sepharose Chromatography," *Agric. Biol. Chem.* 50(5):1333-1334 (1986).
Takahashi, M., et al., "Thermophilic DNA Ligase Purification and Properties of the Enzyme from *Thermus thermophilus* HB8," *Biol. Chem.* 259(16):10041-10047 (1984).
Takahashi, M., et al., Thermophilic HB8 DNA Ligase: Effects of Polyethylene Glycols and Polyamines on Blunt-End Ligation of DNA, *J. Biochem.*, 100:123-31 (1986).
Belgrader et al., "A Multiplex PCR-Ligase Detection Reaction Assay for Human Identity Testing," *Genome Science & Tech.* 1:77-87 (1996).
Newton, "The Production of PCR Products with 5' Single-Stranded Tails Using Primers That Incorporate Novel Phosphoramiclite Intermediates," *Nucleic Acids Research* 21(5):1155-1162 (1993).

\* cited by examiner

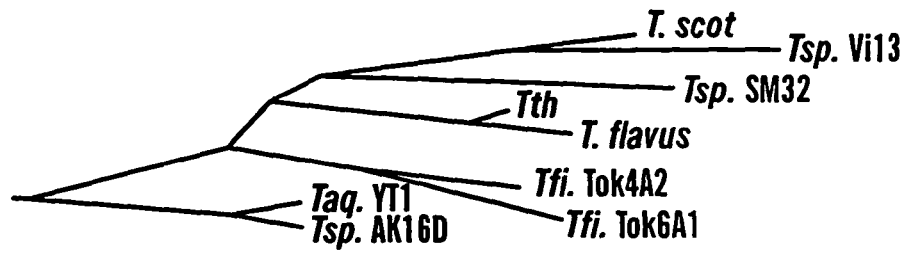

FIG. 1A

| | | | | |
|---|---|---|---|---|
| 113 YTVERKVDGLSVNLYYE 129 | ........ 231 LEE | ... TG 239 | ....... 285 PFEADGVVVKLD 296 | *Tsp.* AK16D |
| YTVEHKVDGLSVNLYYE | ............... LEE | ... TG | ............... PFEADGVVVKLD | *Taq.* YT1 |
| YTVEHKVDGLSVNLYYE | ............... LEEVEREG | | ............... PFEADGVVVKLD | *Tth* |
| YTVEHKVDGLSVNLYYE | ............... LEEVEREG | | ............... PFEADGVVVKLD | *T. flavus* |
| YTVEHKVDGLSVNLYYE | ............... LEE | ... SG | ............... PFEADGVVVKMD | *Tfi.* Tok4A2 |
| YTVEHKVDGLSVNLYYE | ............... LEE | ... SG | ............... PFEADGVVVKLD | *Tfi.* Tok6A1 |
| YTVEHKVDGLSVNLYYE | ............... LEE | ... SG | ............... PFEADGVVVKLD | *Tsp.* SM32 |
| YTVEHKVDGLSVNLYYE | ............... LEE | ... SG | ............... PFEADGVVVKLD | *Tsp.* Vil3 |
| YTVEHKVDGLSVNLYYE | ............... LEE | ... SG | ............... PFEADGVVVKLD | *T. scot* |

FIG. 1B

```
MTLEEARRRVNELRDLIRYHNYLYYVLDAPEISDAEYDRLLRELKELEERFPELKSPDSP      60
TEQVGARPLEATFRPVRHPTRMYSLDNAFSLDEVRAFEERIERALGRKGPFLYTVERKVD     120
GLSVNLYYEEGILVFGATRGDGETGEEVTQNLLTIPTIPRRLTGVPDRLEVRGEVYMPIE     180
AFLRLNQELEEAGERIFKNPRNAAAGSLRQKDPRVTARRGLRATFYALGLGLEETGLKSQ     240
HDLLLWLRERGFPVEHGFTRALGAEGVEEVYQAWLKERRKLPFEADGVVVKLDDLALWRE     300
LGYTARTPRFALAYKFPAEEKETRLLSVAFQVGRTGRITPVGVLEPVFIEGSEVSRVTLH     360
NESFIEELDVRIGDWVLVHKAGGVIPEVLRVLKERRTGEEKPIIWPENCPECGHALIKEG     420
KVHRCPNPLCPAKRFEAIRHYASRKAMDIQGLGEKLIEKLLEKGLVRDVADLYRLKKEDL     480
VNLERMGEKSAENLLRQIEESKGRGLERLLYALGLPGVGEVLARNLALRFGHMDRLLEAG     540
LEDLLEVEGVGELTARAILNTLKDPEFRDLVRRLKEAGVEMEAKEREGEALKGLTFVITG     600
ELSRPREEVKALLRRLGAKVTDSVSRKTSFLVVGENPGSKLEKARALGVPTLSEEELYRL     660
IEERTGKDPRALTA                                                   674
```

FIG. 1C

HIGH FIDELITY THERMOSTABLE LIGASE AND USES THEREOF

This application is a continuation of U.S. patent application Ser. No. 09/830,502 filed Oct. 9, 2001, now U.S. Pat. No. 6,949,370, based on PCT/US99/25437, filed Oct. 29, 1999, allowed, which claims benefit of U.S. Provisional Patent Application Ser. No. 60/106,461 filed Oct. 30, 1998, which are both hereby incorporated by reference in their entirety.

The present invention was made with support under National Institutes of Health Grant Nos. GM-41337-09 and PO1-CA65930-02-04. The U.S. Government may have certain rights.

FIELD OF THE INVENTION

The present invention is directed to a high fidelity mutant thermostable ligase and uses thereof.

BACKGROUND OF THE INVENTION

DNA ligases, as an essential component of DNA replication, recombination, and repair systems found from viruses to humans, catalyze the formation of a phosphodiester bond at single-stranded breaks on duplex DNA (Lehman, I. R., *Science*, 186:790-797 (1974)). DNA ligases can be classified into two families based on cofactor dependence. ATP-dependent ligases are found in bacteriophages (Dunn, et al., *J Mol Biol.*, 148(4):303-330 (1981) and Weiss, et al., *Proc Natl Acad Sci USA*, 57(4):1021-1028 (1967)), Chlorella virus PBCV-1 (Ho, et al., *J Virol*, 71(3):1931-19374 (1997)), Vaccinia virus (Shuman, S., *Biochemistry*, 34(49):16138-161475 (1995)), Archea (Kletzin, A., *Nucleic Acids Res*, 20(20): 5389-5396 (1992) and Bult, et al., *Science*, 273(5278):1058-1073 (1996)), yeasts (Andaluz, et al., *Yeast*, 12(9):893-8988 (1996), Ramos, et al., *Nucleic Acids Res*, 25(8):1485-1492 (1997), Schar, et al., *Genes Dev*, 11 (15):1912-1924 (1997)), mammalian (Tomkinson, et al., *Bioessays*, 19(10):893-901 (1997), Tomkinson, et al., *Mutat Res*, 407(1):1-9 (1998), and Wang, et al., *J Biol Chem*, 269(50):31923-3192811 (1994)), and more recently eubacteria (Cheng, et al., *Nucleic Acids Res*, 25(7): 1369-1374 (1997) and Deckert, et al., *Nature*, 392(6674):353-358 (1998)). $NAD^+$ (i.e. nicotinamide adenine dinucleotide)-dependent ligases, however, are found exclusively in eubacteria. While some higher eucaryotic organisms may use multiple ATP (i.e. adenosine triphosphate)-dependent ligases to fulfill diverse biological functions, some simple eubacteria genomes could host both an $NAD^+$-dependent ligase and an ATP-dependent ligase (Deckert, et al., *Nature*, 392(6674):353-358 (1998) and Fleischmann, et al., *Science*, 269(5223):496-512 (1995)). The origin of the additional ATP-dependent ligases in these genomes remains to be determined.

Although the ATP-dependent ligases and $NAD^+$-dependent ligases share little sequence homology, all the ligases investigated so far use the same KXDG (SEQ. ID. No. 24) motif to form adenylated enzyme intermediate (Tomkinson, et al., *Bioessays*, 19(10):893-901 (1997), Shuman, et al., *Virology*, 211(1):73-83 (1995), and Luo, et al., *Nucleic Acids Res*, 24(15):3079-3085 (1996)). Furthermore, they seem to be organized by similar domains and structural folds ((Doherty, et al., *Nucleic Acids Res*, 24(12):2281-2287 (1996), Subramanya, et al., *Cell*, 85(4):607-615 (1996), and Sekiguchi et al., *Nucleic Acids Res*, 25(4):727-734 (1997)). The diversity of ligase sequences is not only reflected by their different optimal reaction conditions and kinetic rates, but more importantly by their different specificities toward match and mismatch substrates. Among the viral ATP-dependent ligases, the broad substrate tolerance is represented by the T4 enzyme which seals various mismatches on both the 3' and 5' side of the nick junction (Wu, et al., *Gene*, 76(2):245-254 (1989)). Vaccinia ligase ligates various mismatches at both 3'-hydroxyl or 5'-phosphate sides with the exception of purine-purine mismatch pairs at the 3'-hydroxyl side (Shuman, S., *Biochemistry*, 34(49):16138-161475 (1995)). Mammalian ATP-dependent ligases show different substrate sensitivity, as ligase I is more sensitive to 3' mismatches than ligase III (Husain, et al., *J Biol Chem*, 270(16):9683-9690 (1995)). Additionally, both ligase I and III tolerate a 3'C/T mismatch more than a 3'G/T mismatch. Little is known about archeal ATP-dependent ligases which may reveal the nature of the progenitor of ATP-dependent ligases. Studies on $NAD^+$-dependent DNA ligase from *E. coli*, along with T4 ligase, have contributed immensely to understanding of the basic biochemical pathway of the DNA ligation reaction (Lehman, I. R., *Science*, 186(4166):790-797 (1974) and Rossi, et al., *Nucleic Acids Res*, 25(11):2106-2113 (1997)). Studies on the $NAD^+$-dependent ligase from *Thermus thermophilus* HB8 have revealed the highly discriminative power this enzyme possesses (Luo, et al., *Nucleic Acids Res*, 24(15):3071-3078 (1996)). Although mismatches at 5'-phosphate side are tolerated to some degree (5'A/C, 5'A/A, 5'C/A, 5'C/T, 5'G/T, 5'G/A, 5'T/T, 5'T/G), mismatches at the 3'-hydroxyl side essentially abolish nick-closure activity except 3'G/T or 3'T/G mismatch (Luo, et al., *Nucleic Acids Res*, 24(15):3071-3078 (1996)). Apparently, sequence divergence and subsequent subtle structural variation among DNA ligases underlie an enzyme's recognition preferences toward different mismatched base-pairs.

The study of ligase biochemistry is not only important for understanding its biological functions, but also for developing new technologies. The single nucleotide discrimination observed on DNA ligases has led to the development of ligase-mediated detection techniques (Wu, et al., *Gene*, 76(2):245-254 (1989), Wu, et al., *Genomics*, 4(4):560-569 (1989), Landegren, et al., *Science*, 241(4869):1077-1080 (1988), Landegren, U., *Bioessays*, 15(11):761-765 (1993), Barany, F., *PCR Methods Appl*, 1(1):5-16 (1991), and Barany, F., *Proc Natl Acad Sci USA*, 88(1):189-193 (1991)). Ligase-based linear signal amplification known as LDR (i.e. ligase detection reaction), combined with PCR (i.e. polymerase chain reaction)-based gene specific target amplification, has been proven to be a powerful tool in cancer and disease gene mutation detection (Day, et al., *Genomics*, 29(1):152-162 (1995)). PCR/LDR technique relies on two properties of a DNA ligase: (i) specificity and (ii) thermostability. Tth (i.e. *Thermus thermophilus* HB8) DNA ligase has been successfully used in LDR and LCR (i.e. ligase chain reaction) due to its highly discriminative nick closure activity toward a perfect match substrate and its thermostability which makes thermocycling possible (Barany, F., *PCR Methods Appl*, 1(1):5-16 (1991) and Barany, F., *Proc Natl Acad Sci USA*, 88(1):189-193 (1991)). To date, one more ligase was cloned and sequenced from *T. Scot.* (i.e. *Thermus scotoductus*) (Thorbjamardottir, et al., *Gene*, 161(1):1-6 (1995) and Jonsson, et al., *Gene*, 151(1-2):177-180 (1994)), but the substrate specificity of this ligase was not determined.

Despite the existence of a number of ligases from different host sources, the need remains to identify additional ligases with greater fidelity. The present invention is directed to achieving this objective as a result of the cloning and expression of a ligase from T. sp. (i.e. Thermus species) AK16D and the biochemical characterization of this high fidelity enzyme.

SUMMARY OF THE INVENTION

The present invention is directed to a thermostable ligase having 100 fold higher fidelity than T4 ligase and 6 fold higher fidelity than wild-type *Thermus thermophilus* ligase, when sealing a ligation junction between a pair of oligonucleotide probes hybridized to a target sequence where there is a mismatch with the oligonucleotide probe having its 3' end abutting the ligation junction at the base immediately adjacent the ligation junction.

Another aspect of the present invention is directed to a thermostable ligase having 50 fold higher fidelity than T4 ligase and 5 fold higher fidelity than wild-type *Thermus thermophilus* ligase, when sealing a ligation junction between a pair of oligonucleotide probes hybridized to a target sequence where there is a mismatch with the oligonucleotide probe having its 3' end abutting the ligation junction at the base penultimate to the ligation junction.

Yet another aspect of the present invention is directed to a thermostable ligase having, in the presence of a $Mn^{2+}$ cofactor, a 12 fold higher fidelity than wild-type *Thermus thermophilus* ligase, when sealing a ligation junction between a pair of oligonucleotide probes hybridized to a target sequence where there is a mismatch with the oligonucleotide probe having its 3' end abutting the ligation junction at the base immediately adjacent to the ligation junction.

The present invention also relates to a DNA molecule encoding the thermostable ligase as well as expression systems and host cells containing such DNA molecules.

Another aspect of the present invention relates to the use of the thermostable ligase in carrying out a ligase detection reaction process or a ligase chain reaction process.

The ligase detection reaction process, involves detecting a target nucleotide sequence which differs from other nucleotide sequences in the sample by one or more single base changes, insertions, deletions, or translocations. This involves providing a sample potentially containing a target nucleotide sequence which differs from other nucleotide sequences in the sample by one or more single base changes, insertions, deletions, or translocations. The method further includes providing one or more oligonucleotide probe sets, each characterized by (a) a first oligonucleotide probe having a target specific portion and (b) a second oligonucleotide probe having a target-specific portion. The oligonucleotide probes in a particular set are suitable for hybridization to a target nucleotide sequence which differs from other nucleotide sequences in the sample by one or more single base changes, insertions, deletions, or translocations. The probes are also suitable for ligation together when hybridized adjacent to one another on the target nucleotide sequence, but have a mismatch which interferes with such ligation when hybridized to any other nucleotide sequence present in the sample.

The sample, the one or more oligonucleotide probe sets, and the thermostable ligase are blended together to form a ligase detection reaction mixture. The ligase detection reaction mixture is subjected to one or more ligase detection reaction cycles comprising a denaturation treatment and a hybridization treatment. In the denaturation treatment, any hybridized oligonucleotides are separated from the target nucleotide sequence. During the hybridization treatment, the oligonucleotide probe sets hybridize at adjacent positions in a base specific manner to their respective target nucleotide sequences, if present in the sample, and ligate to one another. This forms a ligation product sequence containing the target specific portions connected together with the ligation product sequences for each set being distinguishable from other nucleic acids in the ligase detection reaction mixture. The oligonucleotide probe sets may hybridize to a nucleotide sequence in the sample other than their respective target nucleotide sequences but do not ligate together due to a presence of one or more mismatches and individually separate during the denaturation treatment. The presence of ligation product sequences produced as a result of the target nucleotide sequence being present in the sample is then detected.

In the ligase chain reaction process of the present invention, the presence of a target double stranded nucleic acid formed from first and second complementary target nucleotide sequences is detected in a sample. The target double stranded nucleic acid differs from other nucleotide sequences by one or more single base changes, insertions, deletions, or translocations.

This method involves providing a sample potentially containing a target double stranded nucleic acid formed from first and second complementary nucleotide sequence. This nucleic acid differs from other nucleotide sequences in the sample by one or more single base changes, insertions, deletions, or translocations.

The method further includes providing a first oligonucleotide probe set, characterized by (a) a first oligonucleotide probe having a target specific portion and (b) a second oligonucleotide probe having a target-specific portion. The oligonucleotide probes in the first set are complementary to the first target nucleotide sequence which differs from other nucleotide sequences in the sample by one or more single base changes, insertions, deletions, or translocations. The probes are also suitable for ligation together when hybridized adjacent to one another on the first target nucleotide sequence, but have a mismatch which interferes with such ligation when hybridized to any other nucleotide sequence present in the sample. The method of the present invention also requires providing a second oligonucleotide probe set, characterized by (a) a third oligonucleotide probe having a target specific portion and (b) a fourth oligonucleotide probe having a target-specific portion. The oligonucleotide probes in the second set are complementary to the second target nucleotide sequence which differs from other nucleotide sequences in the sample by one or more single base changes, insertions, deletions, or translocations. The probes of the second set are suitable for ligation together when hybridized adjacent to one another on the second target nucleotide sequence, but have a mismatch which interferes with such ligation when hybridized to any other nucleotide sequence present in the sample.

The sample, the first and second oligonucleotide probe sets, and the thermostable ligase are blended together to form a ligase chain reaction mixture. The ligase chain reaction mixture is subjected to one or more ligase chain reaction cycles comprising a denaturation treatment and a hybridization treatment. During the denaturation treatment, any hybridized oligonucleotides are separated from the target nucleotide sequences. In the hybridization treatment, the oligonucleotide probe sets hybridize at adjacent positions in a base specific manner to their respective target nucleotide sequences, if present in the sample. The probes also ligate to one another to form a ligation product sequence containing the target specific portions connected together with the ligation product sequences for each set being distinguishable from other nucleic acids in the ligase chain reaction mixture. The oligonucleotide probe sets may hybridize to nucleotide sequences in the sample other than their respective target nucleotide sequences but do not ligate together due to a presence of one or more mismatches and individually separate during the denaturation treatment. The presence of ligation product sequences produced as a result of the target nucleotide sequence being present in the sample are then detected.

BRIEF DESCRIPTION OF THE DRAWINGS

FIGS. 1A-C show a sequence comparison of *Thermus* DNA ligases. FIG. 1A illustrates the evolutionary tree for *Thermus* DNA ligases. FIG. 1B is a regional sequence alignment of nine *Thermus* ligases: Tsp. AK16D (SEQ. ID. No. 22); *Thermus aquaticus* YT-1 (SEQ. ID. No. 15); *Thermus Thermophilus* ("Tth") (SEQ. ID. No. 23); *Thermus flavus* (SEQ. ID. No. 16); *Thermus filiformis* Tok4A2 (SEQ. ID. No. 17); *Thermus filiformis* Tok6A1 (SEQ. ID. No. 18); Tsp. SM32 (SEQ. ID. No. 19); Tsp. Vil3 (SEQ. ID. No. 20); *T. scot* (SEQ. ID. No. 21). The aa (i.e. amino acid) sequence of *T. scot* is retrieved from GenBank by accession number 1085749 (SEQ. ID. No. 31). The adenylation motif KXDG (SEQ. ID. No. 24) is underlined and the adenylation site is marked by *. The numbering of aa is based on Tsp. AK16D ligase (SEQ. ID. No. 1). FIG. 1C is a complete amino acid sequence of Tsp. AK16D ligase (SEQ. ID. No. 1). The adenylation motif KXDG (SEQ. ID. No. 24) is underlined and the adenylation site $^{118}$K is shown with a (*) above the residue. The complete sequence of Tsp. AK16D ligase gene and partial sequences of six other *Thermus* ligase genes have been deposited with GenBank under accession No. AF092862 for Tsp. AK16D (SEQ. ID. No. 1), AF092863 (SEQ. ID. No. 25) for *Thermus aquaticus* YT-1, AF092864 (SEQ. ID. No. 26) for *Thermus flavus*, AF092865 (SEQ. ID. No. 27) for *Thermus filiformis* Tok4A2, AF092866 (SEQ. ID. No. 28) for *Thermus filiformis* Tok6A1, AF092867 (SEQ. ID. No. 29) for Tsp. Vil3, and AF092868 (SEQ. ID. No. 30) for Tsp. SM32.

FIG. 3A reveals the pH effect. Reactions were performed in 20 µl mixture containing 200 nM nicked duplex substrate, 12.5 pM Tth ligase or Tsp. AK16D ligase, 20 mM Tris-HCl (pH values were determined at room temperature), 10 mM MgCl$_2$, 100 mM KCl, 10 mM DTT, 1 mM NAD$^+$ and 20 mg/ml BSA at 65° C. for 10 min. FIG. 3B shows the salt effect. Reactions were performed in 20 µl mixture containing 200 nM nicked duplex substrate, 12.5 pM Tth ligase or Tsp. AK16D ligase, 20 mM Tris-HCl, pH 8.5 (at room temperature) for Tth ligase, pH 8.0 for Tsp. AK16D ligase, 10 mM MgCl$_2$, indicated amount of KCl, 10 mM DTT, 1 mM NAD$^+$ and 20 mg/ml BSA at 65° C. for 10 min. FIG. 3C shows the NAD$^+$ effect. Tth ligation reactions were performed in 20 µl mixture containing 200 nM nicked duplex substrate, 12.5 pM Tth ligase and indicated concentration of NAD$^+$, 20 mM Tris-HCl, pH 8.5, 5 mM MgCl$_2$, 100 mM KCl, 10 mM DTT, 1 mM NAD$^+$ and 20 mg/ml BSA at 65° C. for 10 min. Tsp. AK16D ligation reaction were performed in 20 µl mixture containing 200 nM nicked duplex substrate, 12.5 pM Tth ligase and indicated concentration of NAD$^+$, 20 mM Tris-HCl, pH 8.5, 5 mM MgCl$_2$, 50 mM KCl, 10 mM DTT, 1 mM NAD$^+$ and 20 mg/ml BSA at 65° C. for 10 min.

FIG. 4A shows the ligation reactions with different divalent ions as the metal cofactor. FIG. 4B shows the chromatogram of a representative GeneScan gel illustrating ligation product and DNA adenylate intermediate. (−): negative control reactions in which ligase was omitted. Co$^{2+}$ may have caused precipitation of DNA substrate which resulted in disappearance of the unreacted substrate.

FIG. 7A shows the formation of ligated product with gapped and inserted substrates. Reactions were performed in a 20 µl mixture containing 12.5 nM nicked duplex substrate, 1.25 pM Tth ligase or 12.5 nM Tsp. AK16D ligase in the reaction buffer at 65° C. for 4 hours. FIG. 7B shows the proposed reaction path leads to ligation of 1 nt (i.e. nucleotides) inserted substrate.

DETAILED DESCRIPTION OF THE INVENTION

Figure 2:
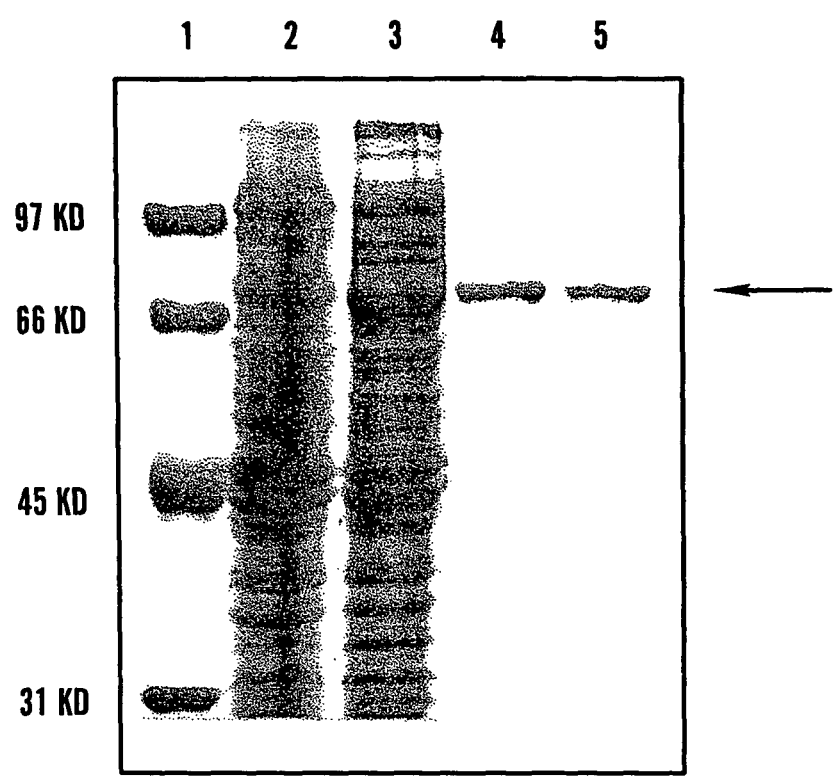
FIG. 2 shows an SDS-PAGE analysis of Tsp. AK16D ligase protein. Lane 1, molecular weight markers; Lane 2, uninduced cell lysate; Lane 3, induced cell lysate; Lane 4, supernatant after heating at 70° C.; Lane 5, fraction eluted from Hitrap blue column. The SDS-polyacrylamide gel was 0.1% SDS-7.5% polyacrylamide and was stained with Coomassie brilliant blue after electrophoresis. The arrow points to the location of Tsp. AK16D ligase.

The present invention relates to a high fidelity thermostable ligase enzyme. This enzyme has the amino acid sequence of SEQ. ID. No. 1 as follows:

MTLEEARRRVNELRDLIRYHNYLYYVLDAPEISDAEYDRLLRELKELEER

FPELKSPDSPTEQVGARPLEATFRPVRHPTRMYSLDNAFSLDEVRAFEER

IEPALGRKGPFLYTVERKVDGLSVNLYYEEGILVFGATRGDGETGEEVTQ

NLLTIPTIPRRLTGVPDRLEVRGEVYMPIEAFLRLNQELEEAGERIFKNP

RNAAAGSLRQKDPRVTARRGLRATFYALGLGLEETGLKSQHDLLLWLRER

GFPVEHGFTPALGAEGVEEVYQAWLKERRKLPFEADGVVVKLDDLALWRE

LGYTARTPRFALAYKFPAEEKETRLLSVAFQVGRTGRITPVGVLEPVFIE

GSEVSRVTLHNESFIEELDVRIGDWVLVHKAGGVIPEVLRVLKERRTGEE

KPIIWPENCPECGHALIKEGKVNRCPNPLCPAKRFEAIRHYASRKAMDIQ

GLGEKLIEKLLEKGLVRDVADLYRLKKEDLVNLERMGEKSAENLLRQIEE

SKGRGLERLLYALGLPGVGEVLARNLALRFGHMDRLLEAGLEDLLEVEGV

GELTARAILNTLKDPEFRDLVRRLKEAGVEMEAKEREGEALKGLTFVITG

ELSRPREEVKALLRRLGAKVTDSVSRKTSFLVVGENPGSKLEKARALGVP

TLSEEELYRLIEERTGKDPRALTA

This protein has a molecular weight of 78 to 81 kDa, as measured by SDS-PAGE. For purposes of the present application, the term "thermostable" refers to a DNA ligase which is resistant to inactivation by heat.

The thermostable ligase of the present invention has a 100 fold higher fidelity than T4 ligase and 6 fold higher fidelity than wild-type *Thermus thermophilus* ligase, when sealing a ligation junction between a pair of oligonucleotide probes hybridized to a target sequence where there is a mismatch with the oligonucleotide probe having its 3' end abutting the ligation junction at the base immediately adjacent the ligation junction. This ligase also has a 50 fold higher fidelity than T4 ligase and 5 fold higher fidelity than wild-type *Thermus thermophilus* ligase, when sealing a ligation junction between a pair of oligonucleotide probes hybridized to a target sequence where there is a mismatch with the oligonucleotide probe having its 3' end abutting the ligation junction at the base penultimate to the ligation junction. Finally, the thermostable ligase of the present invention, in the presence of a $Mn^{2+}$ cofactor, has a 12 fold higher fidelity than wild-type *Thermus thermophilus* ligase, when sealing a ligation junction between a pair of oligonucleotide probes hybridized to a target sequence where there is a mismatch with the oligonucleotide probe having its 3' end abutting the ligation junction at the base immediately adjacent to the ligation junction. For purposes of the present invention, "fidelity" is defined to mean the ratio of the initial rate of ligating two adjacent probes hybridized to a complementary template with a C-G match at the base of the probe with its 3' end at the ligation junction to the initial rate of ligating two adjacent probes hybridized to a complementary template with a G-T mismatch at the base of the probe with its 3' end at the ligation junction.

The thermostable ligase of the present invention is also characterized by having an arginine adjacent to the active site lysine (i.e. K) in the KXDG (SEQ. ID. No. 24) motif (where X is any amino acid).

This protein is encoded by a DNA molecule having a nucleotide sequence of SEQ. ID. No. 2 as follows:

```
ATGACCCTAGAGGAGGCCCGCAGGCGCGTCAACGAACTCAGGGACCTGAT
CCGTTACCACAACTACCTCTATTACGTCTTGGACGCCCCCGAGATCTCCG
ACGCCGAGTACGACCGGCTCCTTAGGGAGCTTAAGGAGCTGGAGGAGCGC
TTTCCCGAGCTCAAAAGCCCCGACTCCCCCACGGAACAGGTGGGGCGAG
GCCTCTGGAGGCCACCTTCCGCCCGGTGCGCCACCCCACCCGCATGTACT
CCCTGGACAACGCCTTTTCCTTGGACGAGGTGAGGGCCTTTGAGGAGCGC
ATAGAGCGGGCCCTGGGGCGGAAGGGGCCCTTCCTCTACACCGTGGAGCG
CAAGGTGGACGGTCTTTCCGTGAACCTCTACTACGAGGAGGGCATCCTCG
TCTTTGGGGCCACCCGGGGCGACGGGGAGACCGGGGAGGAGGTGACCCAG
AACCTCCTCACCATCCCCACCATTCCCCGCCGCCTCACGGGCGTTCCGGA
CCGCCTCGAGGTCCGGGGCGAGGTCTACATGCCCATAGAGGCCTTCCTCA
GGCTCAACCAGGAGCTGGAGGAGGCGGGGAGCGCATCTTCAAAAACCCC
AGGAACGCCGCCGCCGGGTCCTTGCGGCAGAAAGACCCCAGGGTCACGGC
CAGGCGGGGCCTGAGGGCCACCTTTTACGCCCTGGGGCTGGGCCTGGAGG
AAACCGGGTTAAAAAGCCAGCACGACCTTCTCCTATGGCTAAGAGAGCGG
GGCTTTCCCGTGGAGCACGGCTTTACCCGGGCCCTGGGGGCGGAGGGGGT
GGAGGAGGTCTACCAGGCCTGGCTCAAGGAGAGGCGGAAGCTTCCCTTTG
AGGCCGACGGGGTGGTGGTCAAGCTGGACGACCTCGCCCTCTGGCGGGAG
CTGGGGTACACCGCCCGCACCCCCCGCTTCGCCCTCGCCTACAAGTTCCC
GGCCGAGGAGAAGGAGACCCGCCTCCTCTCCGTGGCCTTCCAGGTGGGGC
GGACCGGGCGCATCACCCCCGTGGGCGTTCTGGAGCCCGTCTTCATAGAG
GGCAGCGAGGTGAGCCGGGTCACCCTCCACAACGAGAGCTTCATTGAGGA
GCTGGACGTGCGCATCGGCGACTGGGTGCTGGTCCACAAGGCGGGCGGGG
TGATTCCCGAGGTGCTGAGGGTCCTGAAAGAGCGCCGCACCGGGGAGGAG
AAGCCCATCATCTGGCCCGAGAACTGCCCCGAGTGCGGCCACGCCCTCAT
CAAGGAGGGGAAGGTCCACCGCTGCCCCAACCCCTTGTGCCCCGCCAAGC
GCTTTGAGGCCATCCGCCACTACGCCTCCCGCAAGGCCATGGACATCCAG
GGCCTGGGGGAGAAGCTCATAGAAAAGCTTCTGGAAAAGGGCCTGGTCCG
GGACGTGGCCGACCTCTACCGCCTGAAGAAGGAGGACCTGGTGAACCTGG
AGCGCATGGGGGAGAAGAGCGCAGAGAACCTCCTCCGCCAGATAGAGGAG
AGCAAGGGCCGCGGCCTGGAGCGCCTCCTTTACGCCCTGGGCCTTCCCGG
GGTGGGGGAGGTGCTGGCCCGGAACCTGGCCCTCCCGCTTCGGCCACATGG
ACCGCCTTCTGGAGGCGGGCCTCGAGGACCTCCTGGAGGTGGAGGGGGTG
GGCGAGCTCACCGCCCGGGCCATCCTGAATACCCTAAAGGACCCGGAGTT
CCGGGACCTGGTGCGCCGCCTGAAGGAGGCCGGGGTGGAGATGGAGGCCA
AAGAGCGGGAGGGCGAGGCCTTGAAGGGGCTCACCTTCGTCATCACCGGG
GAGCTTTCCCGGCCCCGGGAGGAGGTGAAGGCCCTCCTTAGGCGGCTTGG
GGCCAAGGTGACGGACTCGGTGAGCCGCAAGACGAGCTTCCTGGTGGTGG
GGGAGAACCCGGGGAGCAAGCTGGAAAAGGCCCGCGCCTTGGGGGTCCCC
ACCCTGAGCGAGGAGGAGCTCTACCGCCTCATTGAGGAGAGGACGGGCAA
GGACCCAAGGGCCCTCACGGCCTAG
```

Fragments of the above polypeptide or protein are also encompassed by the present invention.

Suitable fragments can be produced by several means. In the first, subclones of the gene encoding the protein of the present invention are produced by conventional molecular genetic manipulation by subcloning gene fragments. The subclones then are expressed in vitro or in vivo in bacterial cells to yield a smaller protein or peptide that can be tested for ligase activity according to the procedure described below.

As an alternative, fragments of the ligase of the present invention can be produced by digestion of the full-length ligase with proteolytic enzymes like chymotrypsin or *Staphylococcus* proteinase A, or trypsin. Different proteolytic enzymes are likely to cleave ligase proteins at different sites based on the amino acid sequence of the ligase. Some of the fragments that result from proteolysis may be active ligases.

In another approach, based on knowledge of the primary structure of the protein, fragments of the ligase encoding gene may be synthesized by using the PCR technique together with specific sets of primers chosen to represent particular portions of the protein. These then would be cloned into an appropriate vector for increased expression of a truncated peptide or protein.

Chemical synthesis can also be used to make suitable fragments. Such a synthesis is carried out using known amino acid sequences for the ligase being produced. Alternatively, subjecting the full length ligase to high temperatures and pressures will produce fragments. These fragments can then be separated by conventional procedures (e.g., chromatography, SDS-PAGE).

Variants may also (or alternatively) be modified by, for example, the deletion or addition of amino acids that have minimal influence on the properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

Suitable DNA molecules are those that hybridize to a DNA molecule comprising a nucleotide sequence of 50 continuous bases of SEQ. ID. No. 2 under stringent conditions characterized by a hybridization buffer comprising 0.9M sodium citrate ("SSC") buffer at a temperature of 37° C. and remaining bound when subject to washing with the SSC buffer at 37° C.; and preferably in a hybridization buffer comprising 20% formamide in 0.9M saline/0.09M SSC buffer at a temperature of 42° C. and remaining bound when subject to washing at 42° C. with 0.2×SSC buffer at 42° C.

The protein or polypeptide of the present invention is preferably produced in purified form (preferably at least about 80%, more preferably 90%, pure) by conventional techniques. Typically, the protein or polypeptide of the present invention is secreted into the growth medium of recombinant host cells. Alternatively, the protein or polypeptide of the present invention is produced but not secreted into growth medium. In such cases, to isolate the protein, the host cell (e.g., *E. coli*) carrying a recombinant plasmid is propagated, lysed by sonication, heat, or chemical treatment, and the homogenate is centrifuged to remove bacterial debris. The supernatant is then subjected to sequential ammonium sulfate precipitation. The fraction containing the polypeptide or protein of the present invention is subjected to gel filtration in an appropriately sized dextran or polyacrylamide column to separate the proteins. If necessary, the protein fraction may be further purified by HPLC.

The DNA molecule encoding the ligase of the present invention can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, N.Y. (1989), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promotor which is a DNA sequence that directs the binding of RNA polymerase and thereby promotes mRNA synthesis. The DNA sequences of eucaryotic promotors differ from those of procaryotic promotors. Furthermore, eucaryotic promotors and accompanying genetic signals may not be recognized in or may not function in a procaryotic system, and, further, procaryotic promotors are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference.

Promotors vary in their "strength" (i.e. their ability to promote transcription). For the purposes of expressing a cloned gene, it is desirable to use strong promotors in order to obtain a high level of transcription and, hence, expression of the gene. Depending upon the host cell system utilized, any one of a number of suitable promotors may be used. For instance, when cloning in *E. coli*, its bacteriophages, or plasmids, promotors such as the T7 phage promotor, lac promotor, trp promotor, recA promotor, ribosomal RNA promotor, the $P_R$ and $P_L$ promotors of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promotors produced by recombinant DNA or other synthetic DNA techniques may be used to provide for transcription of the inserted gene.

Bacterial host cell strains and expression vectors may be chosen which inhibit the action of the promotor unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires an SD sequence about 7-9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecule encoding the ligase of the present invention has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

The present invention is useful in a number of processes where a ligase enzyme is conventionally utilized at high temperatures. Generally, these procedures include the ligase detection reaction and the ligase chain reaction.

Both of the ligase detection reaction and ligase chain reaction involve detection of a target sequence and amplification of that sequence at elevated temperatures. In carrying out these procedures, the enzyme is subjected to elevated temperatures but is not degraded due to its thermostable character. The ligase detection reaction and ligase chain reaction procedures are generally described in WO 90/17239 to Barany et. al., F. Barany, et. al., "Cloning, Overexpression, and Nucleotide Sequence of a Thermostable DNA Ligase-Encoding Gene," *Gene* 109: 1-11 (1991), and F. Barany, et. al., "Genetic Disease Detection and DNA Amplification Using Cloned Thermostable Ligase," *Proc. Nat'l Acad. Sci. USA* 88: 189-93, the disclosures of which are hereby incorporated by reference.

The ligase detection reaction process is useful in detecting in a sample a target nucleotide sequence as described more fully below.

One or more oligonucleotide probe sets are provided for use in conjunction with this method. Each set includes (a) a first oligonucleotide probe having a target-specific portion and (b) a second oligonucleotide probe having a target-specific portion. The oligonucleotide probes in a particular set are suitable for ligation together when hybridized adjacent to one another on a corresponding target nucleotide sequence, but have a mismatch which interferes with such ligation when hybridized to any other nucleotide sequence present in the sample.

The sample, the one or more oligonucleotide probe sets, and the ligase are blended to form a ligase detection reaction mixture. The ligase detection reaction mixture is subjected to one or more ligase detection reaction cycles comprising a denaturation treatment and a hybridization treatment. In the denaturation treatment, any hybridized oligonucleotides are separated from the target nucleotide sequences. The hybridization treatment involves hybridizing the oligonucleotide probe sets at adjacent positions in a base-specific manner to the respective target nucleotide sequences, if present in the sample. The hybridized oligonucleotide probes from each set ligate to one another to form a ligation product sequence containing the target-specific portions connected together. The ligation product sequence for each set is distinguishable from other nucleic acids in the ligase detection reaction mixture. The oligonucleotide probe sets may hybridize to adjacent sequences in the sample other than the respective target nucleotide sequences but do not ligate together due to the presence of one or more mismatches. When hybridized oligonucleotide probes do not ligate, they individually separate during the denaturation treatment.

During the ligase detection reaction phase, the denaturation treatment is carried out at a temperature of 80-105° C., while hybridization takes place at 50-85° C. Each cycle comprises a denaturation treatment and a thermal hybridization treatment which in total is from about one to five minutes long. Typically, the ligation detection reaction involves repeatedly denaturing and hybridizing for 2 to 50 cycles. The total time for the ligase detection reaction process is 1 to 250 minutes.

The oligonucleotide probe sets can be in the form of ribonucleotides, deoxynucleotides, modified ribonucleotides, modified deoxyribonucleotides, modified phosphate-sugar-backbone oligonucleotides, nucleotide analogs, and mixtures thereof.

In one variation, the oligonucleotides of the oligonucleotide probe sets each have a hybridization or melting temperature (i.e. $T_m$) of 66-70° C. These oligonucleotides are 20-28 nucleotides long.

The oligonucleotide probe sets, as noted above, have a reporter label suitable for detection. Useful labels include chromophores, fluorescent moieties, enzymes, antigens, heavy metals, magnetic probes, dyes, phosphorescent groups, radioactive materials, chemiluminescent moieties, and electrochemical detecting moieties.

The product of the ligase detection reaction can be detected in either of two formats. These are fully described in WO 98/03673, to Barany et al., which is hereby incorporated by reference. In one of these formats, ligase detection reaction products are detected by capillary or gel electrophoresis. Alternatively, ligation products can be detected on an array by specific hybridization to a complementary sequence on the array.

The ligation detection reaction mixture may include a carrier DNA, such as salmon sperm DNA.

The hybridization step in the ligase detection reaction, which is preferably a thermal hybridization treatment discriminates between nucleotide sequences based on a distinguishing nucleotide at the ligation junctions. The difference between the target nucleotide sequences can be, for example, a single nucleic acid base difference, a nucleic acid deletion, a nucleic acid insertion, or rearrangement. Such sequence differences involving more than one base can also be detected. Preferably, the oligonucleotide probe sets have substantially the same length so that they hybridize to target nucleotide sequences at substantially similar hybridization conditions. As a result, the process of the present invention is able to detect infectious diseases, genetic diseases, and cancer. It is also useful in environmental monitoring, forensics, and food science.

A wide variety of infectious diseases can be detected by the process of the present invention. Typically, these are caused by bacterial, viral, parasite, and fungal infectious agents. The resistance of various infectious agents to drugs can also be determined using the present invention.

Bacterial infectious agents which can be detected by the present invention include *Escherichia coli, Salmonella, Shigella, Klebsiella, Pseudomonas, Listeria monocytogenes, Mycobacterium tuberculosis, Mycobacterium aviumintracellulare, Yersinia, Francisella, Pasteurella, Brucella, Clostridia, Bordetella pertussis, Bacteroides, Staphylococcus aureus, Streptococcus pneumonia*, B-Hemolytic strep., *Corynebacteria, Legionella, Mycoplasma, Ureaplasma, Chlamydia, Neisseria gonorrhea, Neisseria meningitides, Hemophilus influenza, Enterococcus faecalis, Proteus vulgaris, Proteus mirabilis, Helicobacter pylori, Treponema palladium, Borrelia burgdorferi, Borrelia recurrentis, Rickettsial pathogens, Nocardia*, and *Acitnomycetes*.

Fungal infectious agents which can be detected by the present invention include *Cryptococcus neoformans, Blastomyces dermatitidis, Histoplasma capsulatum, Coccidioides immitis, Paracoccidioides brasiliensis, Candida albicans, Aspergillus fumigautus, Phycomycetes (Rhizopus), Sporothrix schenckii, Chromomycosis*, and *Maduromycosis*.

Viral infectious agents which can be detected by the present invention include human immunodeficiency virus, human T-cell lymphocytotrophic virus, hepatitis viruses (e.g., Hepatitis B Virus and Hepatitis C Virus), Epstein-Barr Virus, cytomegalovirus, human papillomaviruses, orthomyxo viruses, paramyxo viruses, adenoviruses, corona viruses, rhabdo viruses, polio viruses, toga viruses, bunya viruses, arena viruses, rubella viruses, and reo viruses.

Parasitic agents which can be detected by the present invention include *Plasmodium falciparum, Plasmodium malaria, Plasmodium vivax, Plasmodium ovale, Onchoverva volvulus, Leishmania, Trypanosoma* spp., *Schistosoma* spp., *Entamoeba histolytica, Cryptosporidum, Giardia* spp., *Trichimonas* spp., *Balatidium coli, Wuchereria bancrofti, Toxoplasma* spp., *Enterobius vermicularis, Ascaris lumbricoides, Trichuris trichiura, Dracunculus medinesis*, trematodes, *Diphyllobothrium latum, Taenia* spp., *Pneumocystis carinii*, and *Necator americanis*.

The present invention is also useful for detection of drug resistance by infectious agents. For example, vancomycin-resistant *Enterococcus faecium*, methicillin-resistant *Staphylococcus aureus*, penicillin-resistant *Streptococcus pneumoniae*, multi-drug resistant *Mycobacterium tuberculosis*, and AZT-resistant human immunodeficiency virus can all be identified with the present invention.

Genetic diseases can also be detected by the process of the present invention. This can be carried out by prenatal or post-natal screening for chromosomal and genetic aberrations or for genetic diseases. Examples of detectable genetic diseases include: 21 hydroxylase deficiency, cystic fibrosis, Fragile X Syndrome, Turner Syndrome, Duchenne Muscular Dystrophy, Down Syndrome or other trisomies, heart disease, single gene diseases, HLA typing, phenylketonuria, sickle cell anemia, Tay-Sachs Disease, thalassemia, Klinefelter Syndrome, Huntington Disease, autoimmune diseases, lipidosis, obesity defects, hemophilia, inborn errors of metabolism, and diabetes.

Cancers which can be detected by the process of the present invention generally involve oncogenes, tumor suppressor genes, or genes involved in DNA amplification, replication, recombination, or repair. Examples of these include: BRCA1 gene, p53 gene, APC gene, Her2/Neu amplification, Bcr/Ab1, K-ras gene, and human papillomavirus Types 16 and 18. Various aspects of the present invention can be used to identify amplifications, large deletions as well as point mutations and small deletions/insertions of the above genes in the following common human cancers: leukemia, colon cancer, breast cancer, lung cancer, prostate cancer, brain tumors, central nervous system tumors, bladder tumors, melanomas, liver cancer, osteosarcoma and other bone cancers, testicular and ovarian carcinomas, head and neck tumors, and cervical neoplasms.

In the area of environmental monitoring, the present invention can be used for detection, identification, and monitoring of pathogenic and indigenous microorganisms in natural and engineered ecosystems and microcosms such as in municipal waste water purification systems and water reservoirs or in polluted areas undergoing bioremediation. It is also possible to detect plasmids containing genes that can metabolize xenobiotics, to monitor specific target microorganisms in population dynamic studies, or either to detect, identify, or monitor genetically modified microorganisms in the environment and in industrial plants.

The present invention can also be used in a variety of forensic areas, including for human identification for military personnel and criminal investigation, paternity testing and family relation analysis, HLA compatibility typing, and screening blood, sperm, or transplantation organs for contamination.

In the food and feed industry, the present invention has a wide variety of applications. For example, it can be used for identification and characterization of production organisms such as yeast for production of beer, wine, cheese, yogurt, bread, etc. Another area of use is with regard to quality control and certification of products and processes (e.g., livestock, pasteurization, and meat processing) for contaminants. Other uses include the characterization of plants, bulbs, and seeds for breeding purposes, identification of the presence of plant-specific pathogens, and detection and identification of veterinary infections.

Desirably, the oligonucleotide probes are suitable for ligation together at a ligation junction when hybridized adjacent to one another on a corresponding target nucleotide sequence due to perfect complementarity at the ligation junction. However, when the oligonucleotide probes in the set are hybridized to any other nucleotide sequence present in the sample, there is a mismatch at a base at the ligation junction which interferes with ligation. Most preferably, the mismatch is at the base at the 3' base at the ligation junction. Alternatively, the mismatch can be at the bases adjacent to bases at the ligation junction.

Before carrying out the ligase detection reaction, in accordance with the present invention, target nucleotide sequences in the sample can be preliminarily amplified. This preferably carried out with polymerase chain reaction. The polymerase chain reaction process is fully described in H. Erlich, et. al, "Recent Advances in the Polymerase Chain Reaction," *Science* 252: 1643-50 (1991); M. Innis, et. al., *PCR Protocols: A Guide to Methods and Applications*, Academic Press: New York (1990) and R. Saiki, et. al., "Primer-directed Enzymatic Amplification of DNA with a Thermostable DNA Polymerase," *Science* 239: 487-91 (1988), which are hereby incorporated by reference.

The ligase detection reaction process achieves linear amplification of a target sequence. The ligase chain reaction utilizes essentially the same steps and conditions as the ligase detection reaction to achieve exponential amplification. This greater level of amplification is achieved by utilizing 2 sets of complementary oligonucleotides with each set hybridizing to complementary strands of a target nucleic acid sequence.

In the ligase chain reaction process of the present invention, the presence of a target double stranded nucleic acid formed from first and second complementary target nucleotide sequences is detected in a sample. The target double stranded nucleic acid differs from other nucleotide sequences by one or more single base changes, insertions, deletions, or translocations.

This method involves providing a sample potentially containing a target double stranded nucleic acid formed from first and second complementary nucleotide sequence. This nucleic acid differs from other nucleotide sequences in the sample by one or more single base changes, insertions, deletions, or translocations.

The method further includes providing a first oligonucleotide probe set, characterized by (a) a first oligonucleotide probe having a target specific portion and (b) a second oligonucleotide probe having a target-specific portion. The oligonucleotide probes in the first set are complementary to the first target nucleotide sequence which differs from other nucleotide sequences in the sample by one or more single base changes, insertions, deletions, or translocations. The probes are also suitable for ligation together when hybridized adjacent to one another on the first target nucleotide sequence, but have a mismatch which interferes with such ligation when hybridized to any other nucleotide sequence present in the sample. The method of the present invention also requires providing a second oligonucleotide probe set, characterized by (a) a third oligonucleotide probe having a target specific portion and (b) a fourth oligonucleotide probe having a target-specific portion. The oligonucleotide probes in the second set are complementary to the second target nucleotide sequence which differs from other nucleotide sequences in the sample by one or more single base changes, insertions, deletions, or translocations. The probes of the second set are suitable for ligation together when hybridized adjacent to one another on the second target nucleotide sequence, but have a mismatch which interferes with such ligation when hybridized to any other nucleotide sequence present in the sample.

The sample, the first and second oligonucleotide probe sets, and the thermostable ligase are blended together to form a ligase chain reaction mixture. The ligase chain reaction mixture is subjected to one or more ligase chain reaction cycles comprising a denaturation treatment and a hybridization treatment. During the denaturation treatment, any hybridized oligonucleotides are separated from the target nucleotide sequences. In the hybridization treatment, the oligonucleotide probe sets hybridize at adjacent positions in a base specific manner to their respective target nucleotide sequences, if present in the sample. The probes also ligate to one another to form a ligation product sequence containing the target specific portions connected together with the ligation product sequences for each set being distinguishable from other nucleic acids in the ligase chain reaction mixture. The oligonucleotide probe sets may hybridize to nucleotide sequences in the sample other than their respective target nucleotide sequences but do not ligate together due to a presence of one or more mismatches and individually separate during the denaturation treatment. The presence of ligation product sequences produced as a result of the target nucleotide sequence being present in the sample are then detected.

EXAMPLES

Example 1

Reagents, Media, and Strains

All routine chemical reagents were purchased from Sigma Chemicals (St. Louis, Mo.) or Fisher Scientific (Fair Lawn, N.J.). Restriction enzymes and T4 DNA ligase were obtained from New England Biolabs (Beverly, Mass.). Oligonucleotide synthesis reagents, DNA sequencing kits, and PCR kits were obtained from Applied Biosystems Division of Perkin-Elmer Corporation (Foster City, Calif.). dNTPs, BSA (i.e. bovine serum albumin), ATP were purchased from Boehringer-Mannheim (Indianapolis, Ind.). Pfu DNA polymerase was purchased from Stratagene (La Jolla, Calif.). *E. coli* strain NovaBlue(DE3)pLysS, and plasmid pET11c were purchased from Novagen, Inc. (Madison, Wis.). Protein assay kit was from Bio-Rad (Hercules, Calif.). HiTrap Blue affinity column was from Pharmacia (Piscataway, N.J.). LB medium was prepared according to standard formula (Sambrook, et al., (1989) *Molecular Cloning-A Laboratory Manual,* 2nd Ed., Cold Spring Harbor Laboratory Press, Cold Spring Harbor, N.Y. (1994), which is hereby incorporated by reference). Sonication buffer consisted of 50 mM Tris-HCl, pH 8.0 and 1 mM EDTA. TE buffer consisted of 10 mM Tris-HCl, pH 8.0 and 1 mM EDTA. Tth DNA ligase and its mutant K294R were purified as previously described (Luo, et al., *Nucleic Acids Res,* 24(15):3071-3078 (1996), which is hereby incorporated by reference).

Example 2

Oligonucleotide Synthesis

Oligonucleotides were synthesized by using a 394 automated DNA synthesizer from Applied Biosystems Division of Perkin-Elmer Corp. PCR and sequencing primers were purified by ethanol precipitation according to instruction manual. The degenerate sense primer 5'-ATC(T/A)(C/G)CGACGC(C/G)GA(G/A)TA(T/C)GA-3' (SEQ. ID. No. 3) corresponding to amino acids 32-38 (ISDAEYD) (SEQ. ID. No. 4) in the *T. thermophilus* HB8 DNA ligase gene, and antisense primers 5'-CC(C/G)GT(C/G)C(G/T)-(G/C)CC(G/C)AC(C/T)TG(A/G)AA-3' (SEQ. ID. No. 5) and 5'-GCCT-TCTC(C/G/A)A(A/G)(T/C)TTG(C/G)(A/T)(G/C)CC-3' (SEQ. ID. No. 6) corresponding to amino acids 333-339 (FQVGRTG) (SEQ. ID. No. 7) and 641-647 (GSKLEKA) (SEQ. ID. No. 8) were used to amplify DNA ligase gene fragments from Thermus strains. Additional PCR and sequencing primers were synthesized as required. PCR amplification primers for cloning Tsp. AK16D DNA ligase gene into pET11c vector were 5'-GCGATTT<u>CATATG</u>ACCCTAGAGGAGGCCCG-3' (SEQ. ID. No. 9) and 5'-GCG<u>GGATCC</u>GAGGC CTTGGAGAAGCTCTT-3', (SEQ. ID. No. 10) where the NdeI and BamHI sites are underlined and the initiation codon in the forward primer is shown in bold. Oligonucleotide substrates for ligation assay were purified on a denaturing sequencing gel (7 M urea/10% polyacrylamide) (Applied Biosystems Inc., The complete guide to evaluating and isolating synthetic oligonucleotides, Applied Biosystems Inc., Foster City, Calif. (1992)). 5'-phosphorylation of oligonucleotides was achieved during synthesis by using Chemical Phosphorylation Reagent (Glen Research, Sterling, Va.). Fluorescent group was attached to a 3'-terminus using Fluorescein CPG column (Glen Research).

Example 3

DNA Amplification, Cloning and Sequence Analysis

Genomic DNAs from *Thermus* strains were isolated as previously described (Cao, et al., *Gene*, 197:205-214 (1997), which is hereby incorporated by reference). PCR amplifications with degenerate and unique primers and inverse PCR on circularized templates were carried out in a GeneAmp PCR System 9700 thermocycler (Applied Biosystems Division of Perkin Elmer) as described (Wetmur, et al., *J Biol Chem*, 269(41):25928-25935 (1994), which is hereby incorporated by reference). The nucleotide sequences of amplified ligase fragments were directly determined on an ABI 373 sequencer using ABI PRISM™ Dye Terminator Cycle Sequencing Ready Reaction Kit (Perkin-Elmer). Full length Tsp. AK16D DNA ligase gene was amplified using PCR amplification primers as described above, digested with NdeI and BamHI, ligated into the cloning vector pET11c treated with the same pair of restriction enzymes, and transformed into *E. coli* strain NovaBlue(DE3)pLysS. Inserts in pET expression vectors were sequenced in both orientations to ensure that the plasmid constructs were free of PCR or ligation error. Nucleic acid and protein sequence analyses were carried out by Clustal method (Higgins, et al., *Comput Appl Biosci*, 5(2): 151-153 (1989), which is hereby incorporated by reference) using MegAlign program of DNASTAR (Madison, Wis.).

Example 4

Expression and Purification of Tsp. AK16D DNA Ligase

*E. coli* NovaBlue(DE3)pLysS cells containing plasmid pTAK encoding the Tsp. AK16D DNA ligase gene from a pET11c construct was propagated overnight at 37° C. in LB medium containing 50 µg/ml ampicillin, 25 µg/ml chloramphenicol, and 0.2% glucose. Overnight cultures were diluted 100-fold into the same medium, grown until the optical density of the culture reached 0.5 at 600 nm, then induced by the addition of IPTG to a final concentration of 1 mM, and grown for an additional 4 hrs under the same conditions. Cells were collected by centrifugation, frozen/thawed at −20° C./23° C., disrupted by sonication, and clarified by centrifugation as previously described (Wetmur, et al., *J Biol Chem*, 269(41): 25928-25935 (1994), which is hereby incorporated by reference). The resulting supernatants were heated at 70° C. for 15 min to denature thermolabile *E. coli* proteins, placed on ice for 30 min to aggregate the denatured proteins, and cleared of denatured proteins by microcentrifugation for 15 min at 4° C. The partially pure DNA ligase was further purified by chromatography using 1 ml HiTrap Blue affinity column. Briefly, the column containing Tsp. AK16D DNA ligase was washed extensively with TE buffer (pH 7.8) containing 0.1 M NaOAc, and the ligase was eluted with TE buffer (pH 7.8) containing 2 M NaCl. After dialysis against TE buffer (pH 8.0) containing 0.2 M KCl and concentration using Centricon-30 (Amicon), protein concentration was assayed by the Bradford method with reagents supplied by Bio-Rad protein assay kit. The amount of protein was determined using BSA as the standard. The purity of the ligase was verified through 7.5% SDS (i.e. sodium dodecyl sulfate)-PAGE (i.e. polyarcylamide gel electrophoresis) analysis followed by visualizing the overloaded gel with routine Coomassie Brilliant Blue R staining.

Example 5

Substrates and Ligation Assay

The oligonucleotide perfect match substrate was formed by annealing two short oligonucleotides (33-mer for LP3'C (SEQ. ID. No. 11) and 30-mer for Com3F (SEQ. ID. No. 12)) with a 59-mer complementary oligonucleotide (Glg). Oligonucleotides LP3'C and Glg (SEQ. ID. No. 14) were in 1.5-fold excess so that the all the 3' Fam labeled Com3F represented nicked substrates (see Luo, et al., *Nucleic Acids Res*, 24(15):3071-3078 (1996), which is hereby incorporated by reference). The T/G mismatch substrate was formed by annealing LP3'T (SEQ. ID. No. 13), which introduced a single base-pair mismatch at the 3'-end of the nick junction, along with Com 3'F to the complementary strand (Glg). The nicked DNA duplex substrates were formed by denaturing DNA probes at 94° C. for 2 min followed by re-annealing at 65° C. for 2 min in ligation buffer. The sequences of the oligonucleotides were listed below (p represents 5' phosphate group):

```
                                            (SEQ. ID. No 12)
pAGTTGTCATAGTTTGATCCTCTAGTCTGGG-Fam-3' Com3FLP3'T (SEQ. ID. No. 13)
5'-CCCTGTTCCAGCGTCTGCGGTGTTGCGTTLP3'C (SEQ. ID. No. 11)
5'-AAAACCCTGTTCCAGCGTCTGCGGTGTTGCGTCGlg (SEQ. ID. No. 14)
3'-GGGACAAGGTCGCAGACGCCACAACGCAGTCAACAGTATCAAACTAG
GAGATCAGACCC5'
```

Ligation mixtures (20 µl) containing indicated amount of DNA ligase and match or mismatch substrate in the ligase buffer (20 mM Tris-HCl, pH 7.6 at room temperature; 10 mM $MgCl_2$; 100 mM KCl; 10 mM DTT (i.e. dithiothreitol); 1 mM $NAD^+$; and 20 mg/ml BSA) were incubated at 65° C. for a predetermined time. Reactions were terminated by the addition of an equal volume of stop solution (i.e. 50 mM EDTA, 80% formamide, and 1% Blue Dextran). Samples (5 µl) were electrophoresed through an 8 M urea-10% polyacrylamide GeneScan gel according to instructional manual (Perkin Elmer). The unreacted substrates were represented by the 30-mer com3F and products were represented by a ligated 63-mer in the case of the match substrate. Both the remaining substrates and ligated products were quantified using GeneScan analysis software 672 (version 2.0, Perkin Elmer).

Example 6

Steady State Kinetics

Steady state kinetic constants were determined by measuring initial rates of the ligation reaction at a given substrate concentration (nicked DNA duplex substrate concentration ranging from 25-400 nM) and a given ligase concentration (12.5 pM for both Tth and Tsp. AK16D) in 100 µl reaction volume at 65° C. A 5 µl aliquot was removed at 0, 2, 4, 6, 8, 10 min, and mixed with 5 µl of stop solution. The remaining substrate was separated from ligated product by GeneScan gel as described above. Initial rates of the ligation reactions were calculated from the generation of ligated product over time. The $K_m$ and $k_{cat}$ values were determined using computer software Ultrafit (Biosoft, Ferguson, Mo.).

Example 7

Sequence Analysis of Seven *Thermus* Ligase Genes

Amino acid sequence alignment of five Gram negative bacterial NAD$^+$-dependent DNA ligases indicates that Tth ligase is 93% identical to *Thermus scotoductus* ligase, 49% to *Rhodothermus marinus* ligase, 48% to *E. coli* ligase, and 38% to *Zymomonas mobilis* based on sequence data retrieved from GeneBank. Degenerate primers corresponding to highly conserved regions of these ligases were used to amplify fragments of ligase genes from seven *Thermus* strains which represent a worldwide collection: *Thermus flavus* from Japan (SEQ. ID. No. 16), *Thermus aquaticus* YT-1 (SEQ. ID. No. 15) and *Thermus* sp. AK16D from Yellowstone National Park in the United States (SEQ. ID. No. 22), *Thermus filiformis* Tok4A2 (SEQ. ID. No. 17) and *Thermus filiformis* Tok6A1 (SEQ. ID. No. 18) from New Zealand, *Thermus* sp. SM32 (SEQ. ID. No. 19) from Azores, and *Thermus* sp. Vil3 (SEQ. ID. No. 20) from Portugal. The sequences of amplified ligase fragments ranging from 1.4 to 1.6 kb were determined by directly sequencing the PCR products using an ABI 373 automated sequencer. *Thermus* ligases, in general, were highly conserved during evolution as demonstrated by 85%-98% sequence identity. In contrast, the amino acid sequences of the restriction endonuclease TaqI and its isoschizomers from the identical strains show only 50-70% aa identities (Cao, et al., *Gene,* 197:205-214 (1997), which is hereby incorporated by reference). Thermus ligases in general show 30-40% sequence identities as compared with DNA ligases from other bacteria. The sequence divergence is slightly higher among the different geographic groups than within the same group, which may reflect random drift or adaptation to their respective local environments (FIG. 1). *Thermus flavus, Thermus filiformis* Tok4A2, *Thermus filiformis* Tok6A1*, Thermus* sp. SM32, *Thermus* sp. Vil3, *Thermus aquaticus* YT-1, and *Thermus* sp. AK16D (SEQ. ID. No. 14) ligases shared 98.2%, 89.9%, 89.5%, 89.8%, 88.3%, 88.2%, 88.1% with *Thermus thermophilus* HB8 DNA ligase, respectively. The adenylation site of the enzymes ($^{118}$KXDG (SEQ. ID. No. 24) where X is in general a hydrophobic residue), as identified by site-directed mutagenesis of Tth DNA ligase, is completely identical among all *Thermus* ligases, furthermore, the flanking sequences of the adenylation motif are also identical except Tsp. AK16D in which the aa residues $^{117}$H before the $^{118}$K is substituted by an $^{117}$R (FIG. 1B). In non-*Thermus* NAD$^+$-dependent ligases discovered to date, the corresponding position is either a Pro or a Leu. The two isolates from Japan can be distinguished from the other *Thermus* strains by a 3-aa-insertion at position 234.

Example 8

Cloning, Expression and Purification of DNA Ligase from Tsp. AK16D

To maximize the chance of finding a Thermus ligase with novel properties, Tsp. AK16D ligase was chosen which showed the least sequence identity as compared with *T. thermophilus* ligase. To obtain the complete sequence of the ORF (i.e. open reading frame), the fragments of the N- and C-terminus of the gene were amplified by inverse PCR and were subject to direct sequencing. The complete ORF of the Thermus sp. AK16D ligase gene consists of 674 amino acids, as compared to 676 aa for Tth ligase and 674 aa for *T. scot* ligase (FIG. 1C). The full-length *Thermus* sp. AK16D ligase gene was PCR amplified using Pfu polymerase and cloned into expression plasmid pET11c (Novagen). The integrity of the insert containing the ligase gene was verified by DNA sequencing. The pET11c plasmid expressing Tsp. AK16D ligase was transformed into competent *E. coli* cells NovaBlue (DE3)pLysS. Production of ligases was induced by adding IPTG to 1 mM final concentration. Tsp. AK16D ligase protein was expressed to approximately 10% of total cellular proteins (FIG. 2, lane 3). Heating at 70° C. for 15 minutes denatured most of *E. coli* proteins while leaving the thermostable ligases as the dominant band (FIG. 2, lane 4). A cibacron blue based affinity chromatography (Pharmacia) further removed residual *E. coli* proteins and nucleic acids, yielding apparently homogenous Tsp. AK16D ligase protein as judged by Coomassie staining (FIG. 2, lane 5).

Example 9

Salt, pH, and NAD$^+$ Dependence of the Ligation Reaction

Figure 3A:
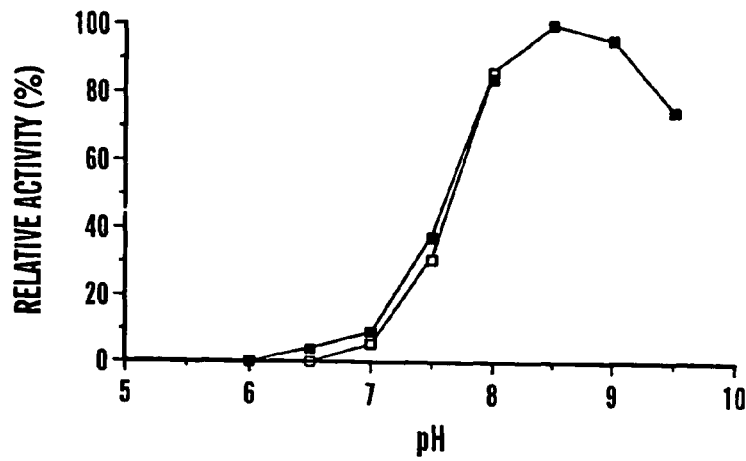
FIGS. 3A-C show the effects of salt, pH, and NAD$^+$ on ligation activity. Tsp. AK16D ligase: closed squares; Tth ligase: open squares.
Figure 3B:
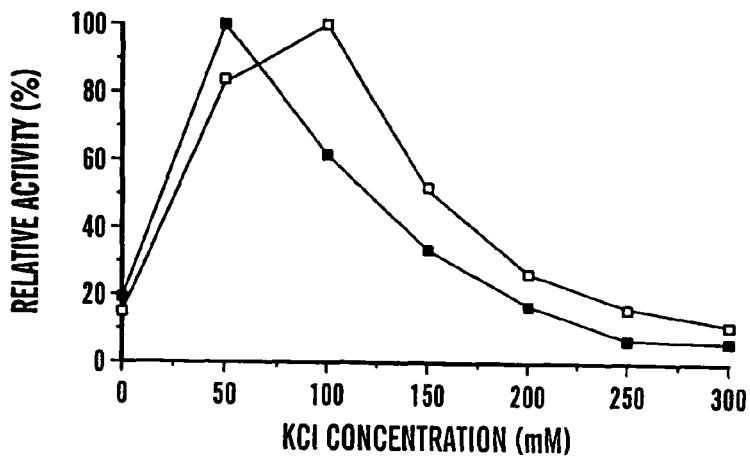
Figure 3C:
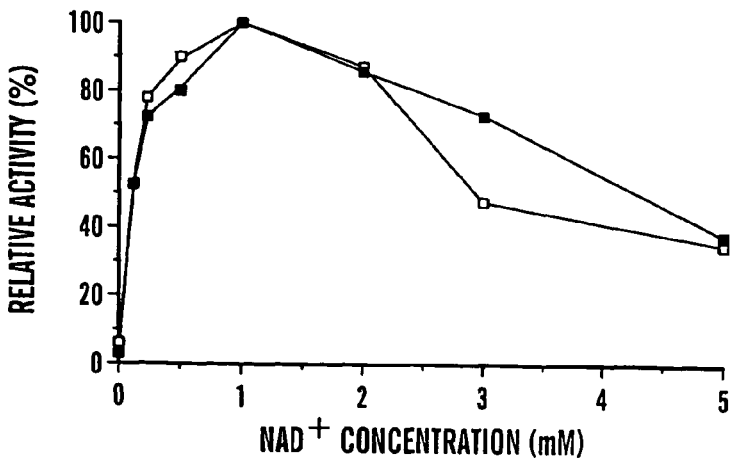

FIG. 3A depicts the pH dependence of ligase activity of Tth and Tsp. AK16D ligase proteins. The shape of the pH dependence curves of Tth ligase and Tsp. AK16D ligase is essentially superimposable. The optimal pH is 8.5 for both Tth ligase and Tsp. AK16D ligase with greater than 80% activity observed between pH 7.8 and 9.5. The identity of pH effect suggests that both of the ligases possess similar local environment at their catalytic center, which is in agreement with the degree of sequence conservation between the two ligases. FIG. 3B depicts the salt concentration dependence of ligase activity of Tth and Tsp. AK16D ligase proteins. The optimum KCl concentration for Tth ligase and Tsp. AK16D ligase are 100 and 50 mM, respectively. FIG. 3C depicts the NAD$^+$ concentration dependence of ligase activity of Tth and Tsp. AK16D proteins. The optimum NAD$^+$ concentration is 1 mM for both Tth ligase and Tsp. AK16D ligase. The similarity of the NAD profiles is in keeping with the highly conserved nature of the N-terminal domain of the ligases which is involved in NAD$^+$ binding.

Example 10

Effects of Divalent Metals on the Ligation Reaction

Figure 4A:
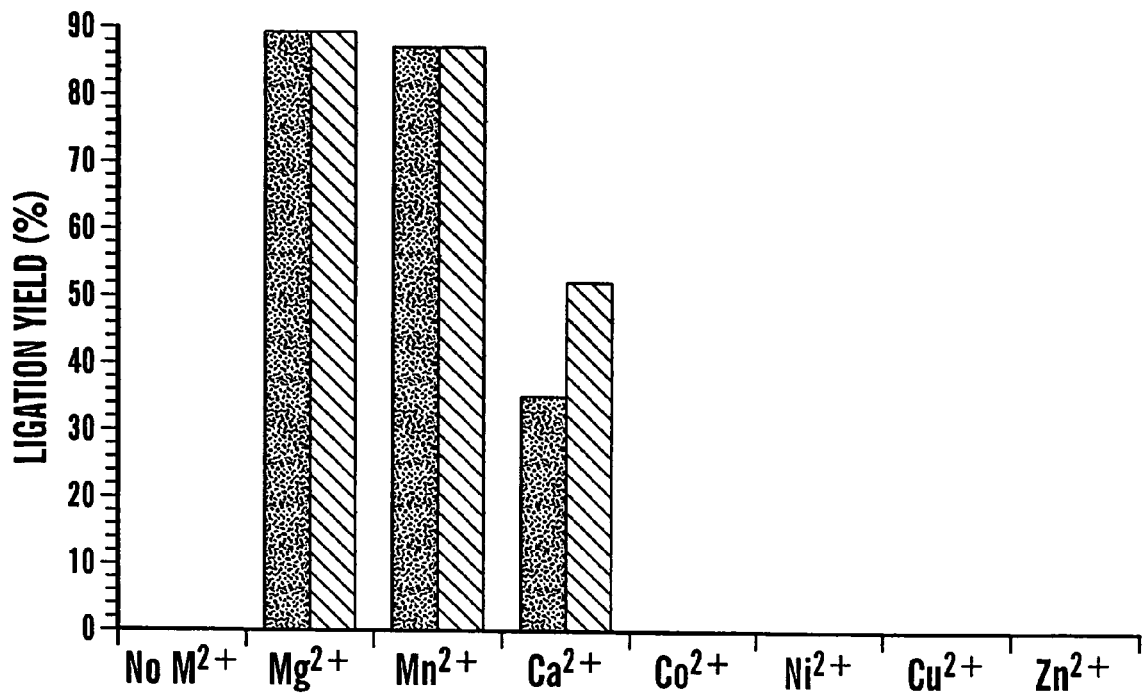
FIGS. 4A-B show the divalent cation dependence of Tsp. AK16D (stripped bars) and Tth (filled bars) ligase activity. Reaction mixtures containing (20 µl) 20 nM nicked duplex substrate, 0.5 nM Tth ligase or 1 nM Tsp. AK16D ligase and 5 mM of indicated divalent cation in the reaction buffers as specified in FIG. 3C were incubated at 65° C. for 10 min.
Figure 4B:
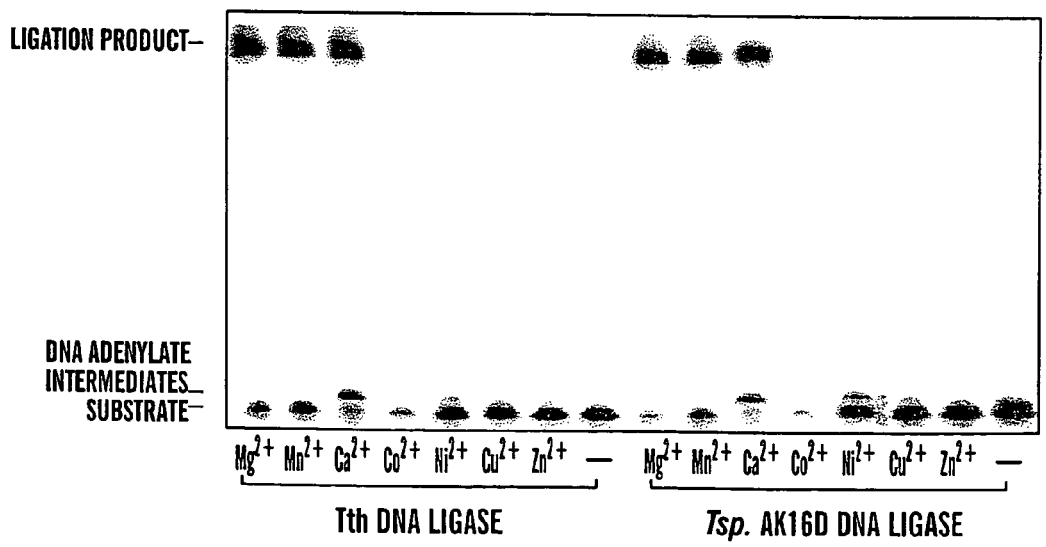
Figure 5A:
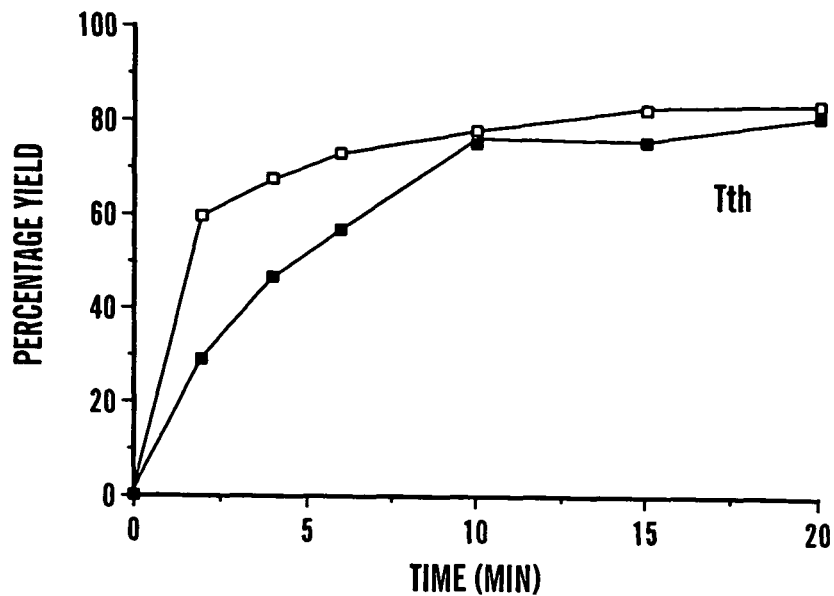
FIGS. 5A-B shows the time course of Tth (FIG. 5A) and Tsp. AK16D (FIG. 5B) ligase activity in the presence of Mg$^{2+}$ (open squares) or Mn$^{2+}$ (closed squares). Reactions were performed in 100 µl mixture containing 20 nM nicked duplex substrate, 0.5 nM Tth ligase or 1 nM Tsp. AK16D ligase and 5 mM Mg$^{2+}$ or Mn$^{2+}$ in the reaction buffers as specified in FIG. 3C at 65° C. Aliquots (5 µl) were removed at the indicated time and reactions stopped by adding equal volumes of stop solution.
Figure 5B:
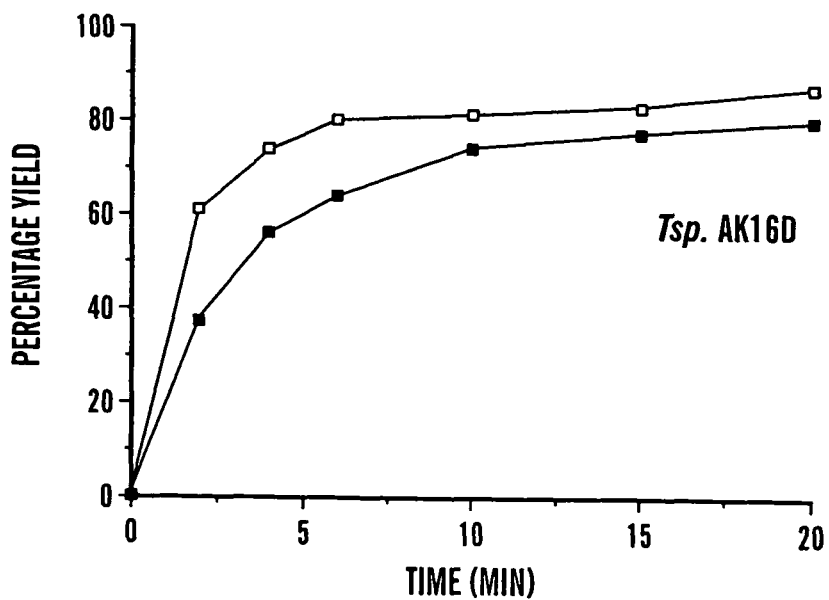
Figure 6A:
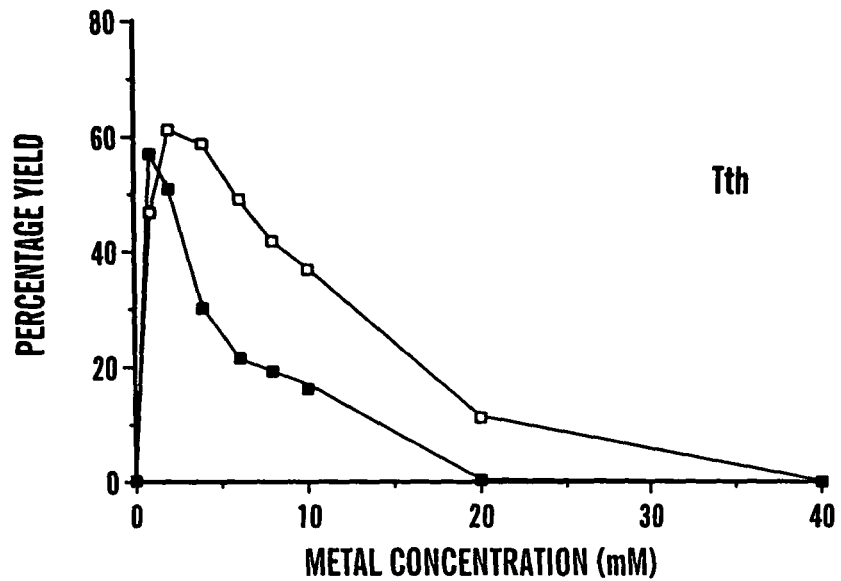
FIGS. 6A-B show the divalent cation concentration dependence of Tth (FIG. 6A) and Tsp. AK16D (FIG. 6B) ligase activity. Mg$^{2+}$ (open squares); Mn$^{2+}$ (closed squares). Reactions were performed in 20 µl mixture containing 20 nM nicked duplex substrate, 0.5 nM Tth ligase or 1 nM Tsp. AK16D ligase and indicated concentration of Mg$^{2+}$ or Mn$^{2+}$ in the reaction buffers as specified in FIG. 4C at 65° C. for 2 min.
Figure 6B:
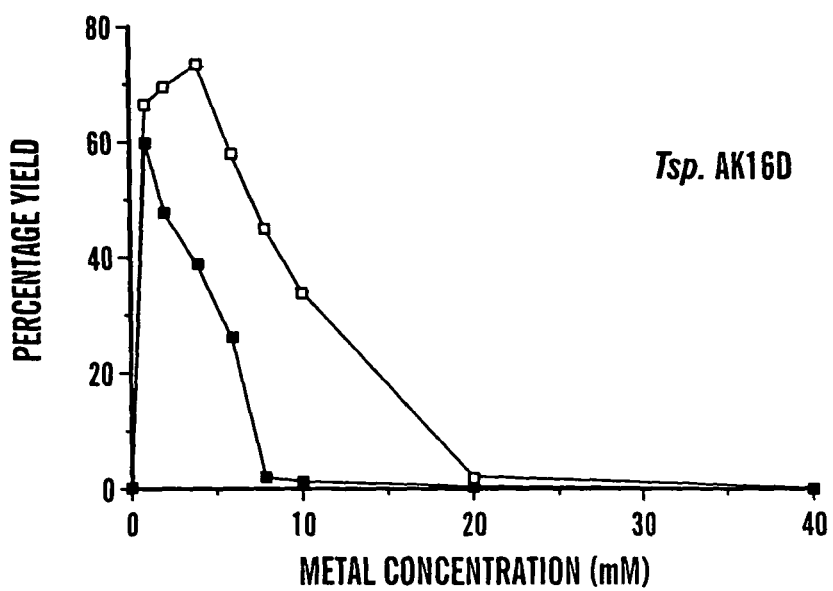

Divalent metal ion is indispensable for each of the three steps in a ligation reaction: (i) adenylation of a lysine residue in the adenylation motif KXDG (SEQ. ID. No. 24); (ii) transfer of the adenylate to the 5' phosphate to form a DNA-adenylate intermediate; and (iii) formation of the phosphodiester bond with the release of adenosine monophosphate (AMP). In general, Mg$^{2+}$ is the preferred metal ion for both ATP-dependent and NAD$^+$-dependent ligases. Mg$^{2+}$ was substituted with alkaline earth metal ion Ca$^{2+}$ and commonly studied period 4 transition metal ions. Tth and Tsp. AK16D ligases could use Mn$^{2+}$ as an alternative metal cofactor to support ligation activity (FIG. 4). Both enzymes were less active with Ca$^{2+}$, while Co$^{2+}$, Ni$^{2+}$, Cu$^{2+}$, and Zn$^{2+}$ failed to support ligation. In comparison, ATP-dependent ligase from Hin (i.e. *Haemophilus influenzae*) uses only Mg$^{2+}$ and Mn$^{2+}$ as the metal cofactor for nick closure but not Ca$^{2+}$, Co$^{2+}$, Cu$^{2+}$, and Zn$^{2+}$ (Cheng, et al., *Nucleic Acids Res,* 25(7):1369-1374 (1997), which is hereby incorporated by reference); ATP-dependent ligase from *Chlorella* virus PBCV-1 can use Mg$^{2+}$, Mn$^{2+}$, and Co$^{2+}$ but not Ca$^{2+}$, Cu$^{2+}$, and Zn$^{2+}$ (Ho, et al., *J Virol,* 71(3):1931-1937 (1997), which is hereby incorporated by reference). Using $Ca^{2+}$ as the metal cofactor, *Thermus* enzymes were able to convert most of the substrate into the DNA-adenylate intermediate. However, the rates of nick closure were reduced which led to the accumulation of the DNA-adenylate intermediate (FIG. 4B). A small amount of the intermediate was observed with $Ni^{2+}$; however, ligation product was not observed at the current detection level, suggesting that $Ni^{2+}$ could not support the nick closure step (FIG. 4B). To further compare the relative activity of the two *Thermus* ligases with $Mg^{2+}$ and $Mn^{2+}$, the generation of ligation product was first monitored over a 20-min time period. As shown in FIG. 5, the *Thermus* enzymes were consistently more active with $Mg^{2+}$ than with $Mn^{2+}$. Second, ligation activity up to 40 mM $Mg^{2+}$ or $Mn^{2+}$ concentrations (FIG. 6) was assayed. Both of the enzymes responded sensitively to the change of the metal ion concentration in the reaction mixture. At high $M^{2+}$ concentrations, the high ionic strength may inhibit the enzyme activity, consistent with KCl dependence profile (FIG. 4). Similar to the time-course results, the *Thermus* enzymes were more active with $Mg^{2+}$ than with $Mn^{2+}$ (FIG. 6). The discrepancy on the relative activity of *Thermus* ligases between this study and an earlier report may be due to use here of cloned enzymes while the earlier work used purified native enzyme (Takahashi, et al., *J Biol Chem,* 259(16):10041-10047 (1984), which is hereby incorporated by reference).

Example 11

Steady State Kinetics

The steady state kinetic constants were measured by monitoring the formation of fluorescently labeled ligation product over time using substrate concentrations spanning estimated Km values (Table 1).

TABLE 1

Steady state kinetics of Tth and Tsp. AK16D ligase[a]

| Ligase | $K_m$ (nM) | $k_{cat}$ (min$^{-1}$) | $k_{cat}/K_m$ (M$^{-1}$ s$^{-1}$) |
|---|---|---|---|
| Tth | 87 | 56 | $1.1 \times 10^7$ |
| Tsp. AK16D | 104 | 38 | $0.62 \times 10^7$ |

[a]Results represent the average of at least three experiments.

The steady state properties of Tsp. AK16D ligase were similar to Tth ligase, indicating that the catalytic channels are highly conserved in *Thermus* ligases. The average Km value of about 90 nM for *Thermus* ligases is similar to the Km value of 50 nM for *E. coli* ligase (Modrich, et al., *J Biol Chem,* 248(21):7495-7501 (1973), which is hereby incorporated by reference) and about 10-fold higher than vaccinia virus ATP-dependent ligase (Sekiguchi, et al., *Nucleic Acids Res,* 25(4): 727-734 (1997), which is hereby incorporated by reference). The average kcat value of about 45 turnovers per min for *Thermus* ligases is higher than the kcat value of 28 turnovers per min for *E. coli* ligase (Modrich, et al., *J Biol Chem,* 248(21):7495-7501 (1973), which is hereby incorporated by reference).

Example 12

Ligation of Gapped or Inserted DNA Duplex Substrates

Figure 7A:
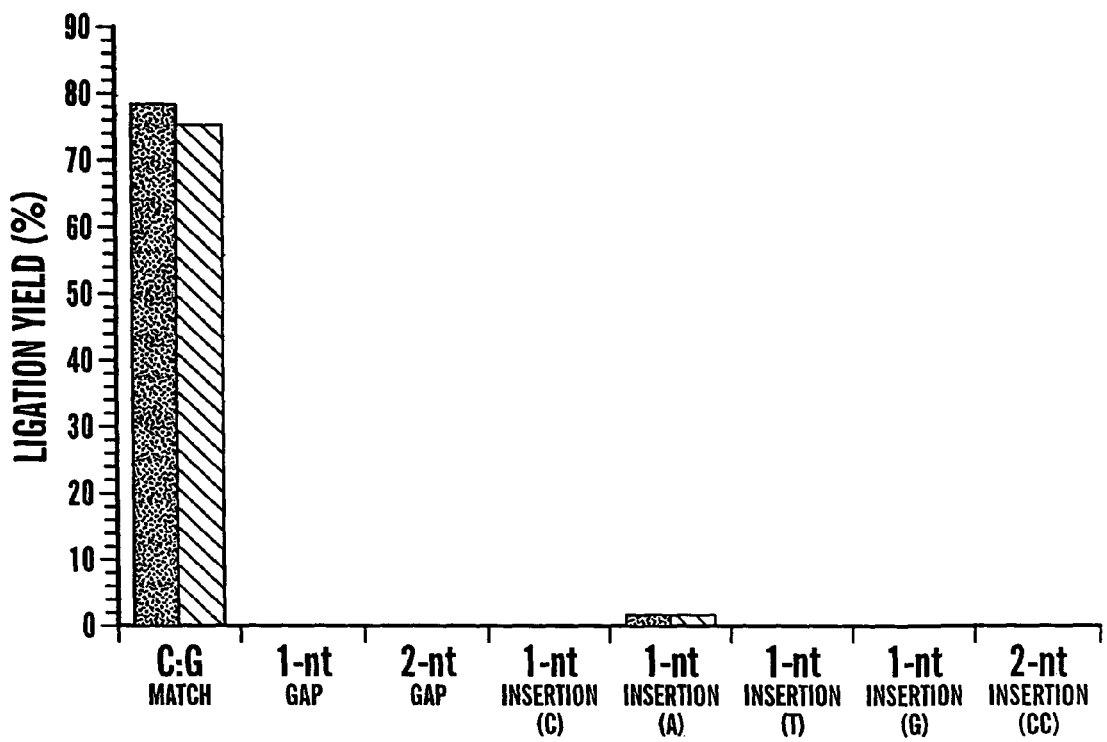
FIGS. 7A-B show the ligation of gapped and inserted substrates.
Figure 7B:
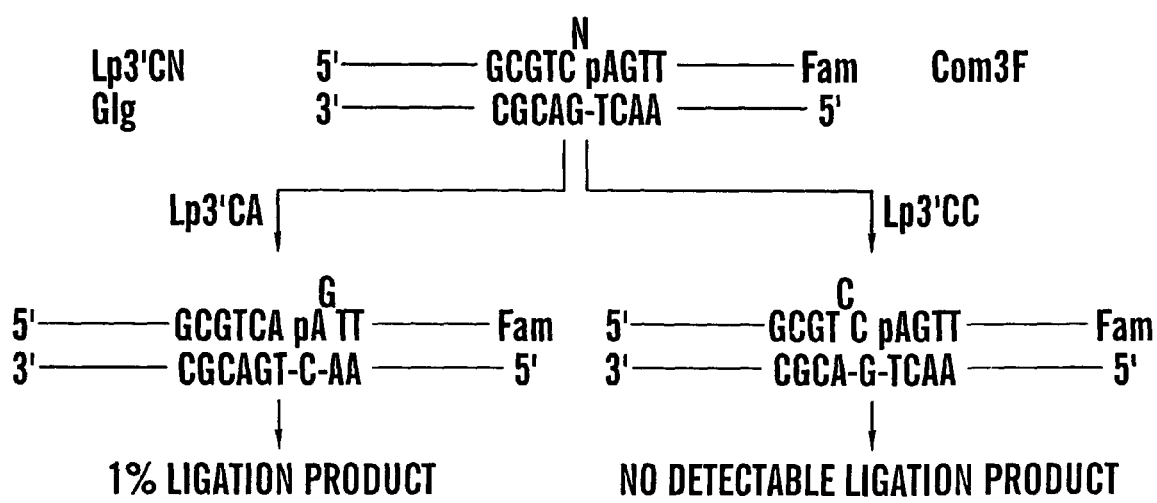

Gapped substrates were formed by deleting one or two nt from the 3' hydroxyl site of oligonucleotide LP3'C, and inserted substrates were formed by adding one or two nt at the 3' hydroxyl site of oligonucleotide LP3'C. Gapped or inserted duplexed DNA sequences are distinctively different from normal nicked substrate. Under our experimental conditions, no ligation was detectable with 1-nt (i.e. nucleotide) or 2-nt gapped or 2-nt insertion substrates for either Tth or Tsp. AK16D ligase (FIG. 7A). As for 1-nt insertion substrates, only A insertion gave a trace amount of ligated products for both ligases (FIG. 7A). All other 1-nt insertions at the ligation junction could not be ligated. In contrast, Hin ligase and *Chlorella ligase* demonstrate observable ligation with 1-nt gap (Ho, et al., *J Virol,* 71(3):1931-1937 (1997) and Cheng, et al., *Nucleic Acids Res,* 25(7):1369-1374 (1997), which are hereby incorporated by reference). In the case of vaccinia ligase, the ligation of 1-nt gap is negligible but the formation of DNA-adenylate intermediate is significant, suggesting the major impact of using 1-nt gapped substrate is on nick closure (Shuman, S., *Biochemistry,* 34(49):16138-16147 (1995), which is hereby incorporated by reference). The formation of DNA-adenylate intermediate with the *Thermus* enzymes was not observed, suggesting that most of the gapped or inserted substrates may have abolished the possibility of completing the second step in the ligation cycle—adenylation of DNA substrate at the 5' phosphate. The 1-nt A insertion mis-ligation could be due to slippage (FIG. 7B). Although *Thermus* ligase slippage is far less than *Thermus* DNA polymerase, it does occur at a low frequency. Given the fact that the adjacent nt is a T, the slippage could have occurred at 5' phosphate side where a 5'A/C mismatch is ligated (Luo, et al., *Nucleic Acids Res,* 24(15):3071-3078 (1996), which is hereby incorporated by reference). It is unlikely that the enzyme tolerates slippage on the 3' side, because a 1 nt C insertion did not yield detectable ligation product (FIG. 7).

Example 13

*Thermus* DNA Ligase Fidelity

Tth DNA ligase is more discriminative when the mismatch is located at the 3' side of the nick junction. 3'G/T or 3'T/G is the only mismatch that shows observable mismatch ligation (Luo, et al., *Nucleic Acids Res,* 24(15):3071-3078 (1996), which is hereby incorporated by reference). To evaluate the fidelity of the cloned Tsp. AK16D ligase, the rate ratio of match over 3'T/G mismatch ligation was compared with wild-type and K294R mutant Tth DNA ligases along with T4 ligase from a commercial source (Table 2).

TABLE 2

DNA ligase fidelity[a]

| Ligase | Enzyme Concentration (nM) | Initial rates of C-G match (fmol/min) | Initial rates of T-G mismatch at 3'-end (fmol/min) | Initial rates of T-G mismatch at penultimate 3'-end (fmol/min) | Ligation fidelity 1[b] | Ligation fidelity 2[c] |
|---|---|---|---|---|---|---|
| T4 | 0.5 | $1.4 \times 10^2$ | 2.8 | 7.1 | $5.0 \times 10^1$ | $1.9 \times 10^1$ |
| Tth-wt | 1.25 | $5.5 \times 10^1$ | $6.5 \times 10^{-2}$ | $2.9 \times 10^{-1}$ | $8.4 \times 10^2$ | $1.9 \times 10^2$ |

TABLE 2-continued

DNA ligase fidelity[a]

| Tth-K294R | 12.5 | $1.5 \times 10^2$ | $2.3 \times 10^{-2}$ | $4.3 \times 10^{-1}$ | $6.3 \times 10^3$ | $3.4 \times 10^2$ |
|---|---|---|---|---|---|---|
| Tsp.AK16D | 12.5 | $1.3 \times 10^2$ | $2.5 \times 10^{-2}$ | $1.2 \times 10^{-1}$ | $5.1 \times 10^3$ | $1.1 \times 10^3$ |

[a]The reaction mixture consisted of 12.5 nM nicked DNA duplex substrates, indicated the amount of DNA ligases in ligation reaction buffer. T4 DNA ligase fidelity was assayed at 37° C., thermophilic ligase fidelity was assayed at 65° C. Five µl Aliquots from a 160 µl reaction mixture were removed at 0, 10, 20, 30, 40, 50, 60 s for reactions containing matched substrates and at 0, 1, 2, 3, 4, 5, 6 h for reactions containing mismatched substrates, and mixed with 5 µl of stop solution. Samples (5 µl) were electrophoresed through an 8M urea-10% polyacrylamide gel as described. Fluorescently labeled ligation products were analyzed and quantified using Genescan 672 version 2.0 software (Applied Biosystems, Foster City, CA). The results were plotted using DeltaGraph Pro3 software (DeltaPoint Inc., Monterey, CA). The initial rates were determined as the slope of linear range of the graph with the x-axis as the time and the y-axis as the amount of the ligation product generated. A schematic illustration of matched and mismatched substrates are as follows:
C-G match at 3'-end  T-G mismatch at 3'-end  T-G mismatch at penultimate 3'-end
—GTC p—F            —GTT p—F               —GTC p—F
—CAG—               —CAG—                  —CGG—
[b]Ligation fidelity 1 = Initial Rate of C-G match/Initial Rate of T-G mismatch at 3'-end.
[c]Ligation fidelity 2 = Initial Rate of C-G match/Initial Rate of T-G mismatch at penultimate 3'-end. The concentrations of DNA ligases used in each experiment are as indicated. Results were calculated as the average of at least two experiments.

T4 ligase demonstrated high catalytic efficiency toward both match and 3'T/G mismatch substrate such that a ligation fidelity of 50 was obtained. *Thermus* ligases appeared to be less efficient in match ligation as evidenced by the requirement of higher enzyme concentration to achieve comparable match ligation rate. However, under the same assay conditions, *Thermus* enzymes were far less prone to ligate a 3'T/G mismatch. As a result, the fidelity of *Thermus* enzymes was 17- to 126-fold higher than T4 ligase (Table 2, Ligation fidelity 1). The fidelity of the newly cloned Tsp. AK16D ligase was similar to K294R Tth mutant but 6-fold higher than wild-type Tth enzyme. A DNA-adenylate intermediate was observed with 3'T/G mismatch ligation, suggesting that a mismatch at the 3' ligation junction imposes substantial constraints on the ability of *Thermus* ligases to close the nick, thereby limiting the turnover of DNA-adenylate intermediate into ligated product and free AMP (the third step of ligation cycle). The effects of moving the T/G mismatch one base-pair away from the ligation junction was further examined. The rates of ligation with a T/G mismatch at the penultimate 3' end in general improved several-fold as compared with the T/G mismatch at the 3' end of the ligation junction. However, the ligation rates were still much slower than those of match ligation, emphasizing the importance of nucleotide complementarity near the ligation junction as well as the ultimate critical role of the perfect base-pair at the 3' end in controlling ligation reaction. Consequently, the ligation fidelity when the mismatch was at the second position from the 3' side (ligation fidelity 2) was lower than that when the mismatch was located immediately at the ligation junction. It is noteworthy that the Tsp. AK16D enzyme maintains extremely high fidelity ($1.1 \times 10^3$) even when the mismatch is at the penultimate position, further underscoring the discriminative power of this new *Thermus* ligase.

Example 14

Thermostable DNA Ligase Fidelity in the Presence of $Mn^{2+}$

Many enzymes such as DNA polymerase and restriction endonucleases demonstrate relaxed specificity when $Mn^{2+}$ is used as the metal cofactor. The influence of metal ion substitution on ligase fidelity has not been fully investigated although it is known that $Mn^{2+}$ can be used as an alternative metal cofactor for a ligation reaction ((Ho, et al., *J Virol*, 71(3):1931-1937 (1997) and Cheng, et al., *Nucleic Acids Res*, 25(7):1369-1374 (1997), which are hereby incorporated by reference). The reaction rates of the match and mismatch ligation for Tsp. AK16D ligase and Tth ligase were determined. As shown in Table 3, the match ligation rates were higher with $Mg^{2+}$ than with $Mn^{2+}$ (Table 3), in agreement with the consistent high ligation rate under various $Mg^{2+}$ conditions (FIG. 4-6).

TABLE 3

DNA ligase fidelity with $Mn^{2+a}$

| Ligase | Concentration (nM) | Initial rate of C-G match (fmol/min) | Initial rate of T-G mismatch (fmol/min) | Ligation fidelity |
|---|---|---|---|---|
| Tth-wt | 1.25 | $2.6 \times 10^1$ | $3.7 \times 10^{-1}$ | $7.0 \times 10^1$ |
| Tsp. AK16D | 12.5 | $9.5 \times 10^1$ | $1.1 \times 10^{-1}$ | $8.6 \times 10^2$ |

[a]Reaction conditions were identical to those in Table 2, except that 10 mM $Mn^{2+}$ was used in place of $Mg^{2+}$. Ligation fidelity was defined as the ratio of Initial Rate of C-G match divided by Initial Rate of T-G mismatch at 3'-end. Results were calculated as the average of at least two experiments.

The mismatch ligation rate of Tth ligase was about six-fold higher with $Mn^{2+}$ than with $Mg^{2+}$ while that of Tsp. AK16D ligase was about 4-fold higher. Thus, as with other previously studied DNA enzymes, DNA ligases also demonstrate relaxed specificity when $Mg^{2+}$ is substituted with $Mn^{2+}$. As a result, the fidelity factors of Tth ligase and Tsp. AK16D ligase were reduced 12- and 6-fold, respectively (Tables 2-3). Remarkably, the Tsp. AK16D enzyme retains 12-fold higher fidelity against mismatch ligation than the Tth enzyme. In contrast to using $Mg^{2+}$ as the metal cofactor, Tth ligase did not generate DNA-adenylate intermediate during 3'T/G mismatch ligation with $Mn^{2+}$. This observation suggests that the nick closure of a 3'T/G mismatch by the Tth enzyme is accelerated with $Mn^{2+}$. On the other hand, the Tsp. AK16D enzyme accumulated DNA-adenylate intermediate during 3'T/G mismatch ligation with either $Mg^{2+}$ or $Mn^{2+}$. These results indicate that the nick closure of a 3'T/G mismatch with Mn$^{2+}$ by Tsp. AK16D DNA ligase remains as the rate-limiting step, which accounts for the higher fidelity of this enzyme.

Studies on Tth DNA ligase has deepened understanding of thermostable ligases and has reaffirmed the common theme of ligation—adenylation of ligase at the KXDG (SEQ. ID. No. 24) motif (Luo, et al., *Nucleic Acids Res,* 24(15):3079-3085 (1996), which is hereby incorporated by reference). This study reveals that *Thermus* ligases may differ from each other as to substrate specificity despite their highly identical primary protein sequences. A highly homologous structure can be anticipated from various *Thermus* ligases, but subtle local environments may dictate the probability of accepting a particular mismatch as the substrate. The fidelity of the *Thermus* ligases may be determined by multiple domains, multiple motifs and/or multiple sequence elements. In comparison of Tth and Tsp. AK16D ligases, one can find that although K294R (in an identical local environment, see FIG. 1B) enhances the fidelity of Tth ligase (Luo, et al., *Nucleic Acids Res,* 24(15):3071-3078 (1996), which is hereby incorporated by reference), Tsp. AK16D ligase with a K in this position can still demonstrate superior mismatch discrimination. Additional sequence elements remain to be uncovered. The R substitution at the adjacent position to the KXDG (SEQ. ID. No. 24) motif may have an effect on the Tsp. AK16D ligase's specificity, because studies on *Chlorella* ligase has emphasized the importance of occupying AMP binding pocket for nick recognition (Sriskanda, et al., *Nucleic Acids Res,* 26(2): 525-531 (1998)). The accumulation of DNA-adenylate intermediate with some divalent metal ions by Tsp. AK16D ligase asserts that the nick closure step of a ligation reaction can be sensitive to the selection of metal ions, gapped substrates and mismatch substrates. More structural and functional studies on Tsp. AK16D ligase could reveal how this enzyme achieves high fidelity with different substrates and different metal ions.

Although the invention has been described in detail for the purpose of illustration, it is understood that such details are solely for that purpose and that variations can be made therein by those skilled in the art without departing from the spirit of the scope of the invention which is defined by the following claims.

What is claimed:

1. An isolated thermostable ligase, wherein the ligase is a mutant of a wild-type thermostable ligase, said wild-type thermostable ligase having a histidine adjacent to a KVDG motif, wherein the mutant thermostable ligase has a histidine to arginine mutation in its amino acid sequence at the histidine adjacent to the KVDG motif in the wild-type thermostable ligase, wherein the wild-type DNA ligase comprises the amino acid sequence of SEQ ID NO: 25.

* * * * *

SEQUENCE LISTING

<160> NUMBER OF SEQ ID NOS: 31

<210> SEQ ID NO 1
<211> LENGTH: 674
<212> TYPE: PRT
<213> ORGANISM: Thermus sp.

<400> SEQUENCE: 1

```
Met Thr Leu Glu Glu Ala Arg Arg Val Asn Glu Leu Arg Asp Leu
 1               5                  10                  15

Ile Arg Tyr His Asn Tyr Leu Tyr Tyr Val Leu Asp Ala Pro Glu Ile
                20                  25                  30

Ser Asp Ala Glu Tyr Asp Arg Leu Leu Arg Glu Leu Lys Glu Leu Glu
            35                  40                  45

Glu Arg Phe Pro Glu Leu Lys Ser Pro Asp Ser Pro Thr Glu Gln Val
        50                  55                  60

Gly Ala Arg Pro Leu Glu Ala Thr Phe Arg Pro Val Arg His Pro Thr
65                  70                  75                  80

Arg Met Tyr Ser Leu Asp Asn Ala Phe Ser Leu Asp Glu Val Arg Ala
                85                  90                  95

Phe Glu Glu Arg Ile Glu Arg Ala Leu Gly Arg Lys Gly Pro Phe Leu
            100                 105                 110

Tyr Thr Val Glu Arg Lys Val Asp Gly Leu Ser Val Asn Leu Tyr Tyr
        115                 120                 125

Glu Glu Gly Ile Leu Val Phe Gly Ala Thr Arg Gly Asp Gly Glu Thr
    130                 135                 140

Gly Glu Glu Val Thr Gln Asn Leu Leu Thr Ile Pro Thr Ile Pro Arg
145                 150                 155                 160

Arg Leu Thr Gly Val Pro Asp Arg Leu Glu Val Arg Gly Glu Val Tyr
                165                 170                 175

Met Pro Ile Glu Ala Phe Leu Arg Leu Asn Gln Glu Leu Glu Glu Ala
            180                 185                 190

Gly Glu Arg Ile Phe Lys Asn Pro Arg Asn Ala Ala Ala Gly Ser Leu
        195                 200                 205

Arg Gln Lys Asp Pro Arg Val Thr Ala Arg Arg Gly Leu Arg Ala Thr
    210                 215                 220
```

```
Phe Tyr Ala Leu Gly Leu Gly Leu Glu Glu Thr Gly Leu Lys Ser Gln
225                 230                 235                 240

His Asp Leu Leu Leu Trp Leu Arg Glu Arg Gly Phe Pro Val Glu His
            245                 250                 255

Gly Phe Thr Arg Ala Leu Gly Ala Glu Gly Val Glu Val Tyr Gln
        260                 265                 270

Ala Trp Leu Lys Glu Arg Arg Lys Leu Pro Phe Glu Ala Asp Gly Val
            275                 280                 285

Val Val Lys Leu Asp Asp Leu Ala Leu Trp Arg Glu Leu Gly Tyr Thr
290                 295                 300

Ala Arg Thr Pro Arg Phe Ala Leu Ala Tyr Lys Phe Pro Ala Glu Glu
305                 310                 315                 320

Lys Glu Thr Arg Leu Leu Ser Val Ala Phe Gln Val Gly Arg Thr Gly
                325                 330                 335

Arg Ile Thr Pro Val Gly Val Leu Glu Pro Val Phe Ile Glu Gly Ser
                340                 345                 350

Glu Val Ser Arg Val Thr Leu His Asn Glu Ser Phe Ile Glu Glu Leu
            355                 360                 365

Asp Val Arg Ile Gly Asp Trp Val Leu Val His Lys Ala Gly Gly Val
370                 375                 380

Ile Pro Glu Val Leu Arg Val Leu Lys Glu Arg Arg Thr Gly Glu Glu
385                 390                 395                 400

Lys Pro Ile Ile Trp Pro Glu Asn Cys Pro Glu Cys Gly His Ala Leu
                405                 410                 415

Ile Lys Glu Gly Lys Val His Arg Cys Pro Asn Pro Leu Cys Pro Ala
            420                 425                 430

Lys Arg Phe Glu Ala Ile Arg His Tyr Ala Ser Arg Lys Ala Met Asp
            435                 440                 445

Ile Gln Gly Leu Gly Glu Lys Leu Ile Glu Lys Leu Leu Glu Lys Gly
                450                 455                 460

Leu Val Arg Asp Val Ala Asp Leu Tyr Arg Leu Lys Lys Glu Asp Leu
465                 470                 475                 480

Val Asn Leu Glu Arg Met Gly Glu Lys Ser Ala Glu Asn Leu Leu Arg
                485                 490                 495

Gln Ile Glu Glu Ser Lys Gly Arg Gly Leu Glu Arg Leu Leu Tyr Ala
                500                 505                 510

Leu Gly Leu Pro Gly Val Gly Glu Val Leu Ala Arg Asn Leu Ala Leu
            515                 520                 525

Arg Phe Gly His Met Asp Arg Leu Leu Glu Ala Gly Leu Glu Asp Leu
            530                 535                 540

Leu Glu Val Glu Gly Val Gly Glu Leu Thr Ala Arg Ala Ile Leu Asn
545                 550                 555                 560

Thr Leu Lys Asp Pro Glu Phe Arg Asp Leu Val Arg Arg Leu Lys Glu
                565                 570                 575

Ala Gly Val Glu Met Glu Ala Lys Glu Arg Glu Gly Glu Ala Leu Lys
            580                 585                 590

Gly Leu Thr Phe Val Ile Thr Gly Glu Leu Ser Arg Pro Arg Glu Glu
            595                 600                 605

Val Lys Ala Leu Leu Arg Arg Leu Gly Ala Lys Val Thr Asp Ser Val
610                 615                 620

Ser Arg Lys Thr Ser Phe Leu Val Val Gly Glu Asn Pro Gly Ser Lys
625                 630                 635                 640

Leu Glu Lys Ala Arg Ala Leu Gly Val Pro Thr Leu Ser Glu Glu Glu
                645                 650                 655
```

Leu Tyr Arg Leu Ile Glu Glu Arg Thr Gly Lys Asp Pro Arg Ala Leu
           660                 665                 670

Thr Ala

<210> SEQ ID NO 2
<211> LENGTH: 2025
<212> TYPE: DNA
<213> ORGANISM: Thermus sp.

<400> SEQUENCE: 2

| | | | |
|---|---|---|---|
| atgaccctag aggaggcccg caggcgcgtc aacgaactca gggacctgat ccgttaccac | | | 60 |
| aactacctct attacgtctt ggacgccccc gagatctccg acgccgagta cgaccggctc | | | 120 |
| cttagggagc ttaaggagct ggaggagcgc tttcccgagc tcaaaagccc cgactccccc | | | 180 |
| acggaacagg tggggcgag gcctctggag gccaccttcc gcccggtgcg ccaccccacc | | | 240 |
| cgcatgtact ccctggacaa cgccttttcc ttggacgagg tgaggccctt gaggagcgc | | | 300 |
| atagagcggg ccctggggcg aaggggccc ttcctctaca ccgtggagcg caaggtggac | | | 360 |
| ggtcttttccg tgaacctcta ctacgaggag gcatcctcg tctttgggc cacccggggc | | | 420 |
| gacggggaga ccggggagga ggtgacccag aacctcctca ccatccccac cattccccgc | | | 480 |
| cgcctcacgg gcgttccgga ccgctcgag gtccggggcg aggtctacat gcccatagag | | | 540 |
| gccttcctca ggctcaacca ggagctggag gaggcggggg agcgcatctt caaaaacccc | | | 600 |
| aggaacgccg ccgccgggtc cttgcggcag aaagacccca gggtcacggc caggcggggc | | | 660 |
| ctgagggcca ccttttacgc cctggggctg gcctggagg aaaccgggtt aaaaagccag | | | 720 |
| cacgaccttc tcctatggct aagagagcgg ggctttcccg tggagcacgg ctttacccgg | | | 780 |
| gccctggggg cggaggggt ggaggaggtc taccaggcct ggctcaagga gaggcggaag | | | 840 |
| cttccctttg aggccgacgg ggtggtggtc aagctgacg acctcgccct ctggcgggag | | | 900 |
| ctggggtaca ccgcccgcac ccccgcttc gccctcgcct acaagttccc ggccgaggag | | | 960 |
| aaggagaccc gctcctctc cgtgccttc caggtgggc ggaccggggcg catcaccccc | | | 1020 |
| gtgggcgttc tggagcccgt cttcatagag ggcagcgagg tgagccgggt caccctccac | | | 1080 |
| aacgagagct tcattgagga gctggacgtg cgcatcggcg actgggtgct ggtccacaag | | | 1140 |
| gcgggcggg tgattcccga ggtgctgagg gtcctgaaag agcgccgcac cggggaggag | | | 1200 |
| aagcccatca tctggcccga gaactgcccc gagtgcggcc acgccctcat caaggagggg | | | 1260 |
| aaggtccacc gctgccccaa ccccttgtgc cccgccaagc gctttgaggc catccgccac | | | 1320 |
| tacgcctccc gcaaggccat ggacatccag ggcctggggg agaagctcat agaaaagctt | | | 1380 |
| ctggaaaagg gcctggtccg ggacgtggcc gacctctacc gcctgaagaa ggaggacctg | | | 1440 |
| gtgaacctgg agcgcatggg ggagaagagc gcagagaacc tcctccgcca gatagaggag | | | 1500 |
| agcaagggcc gcgcctgga gcgcctcctt tacgccctgg ccttcccgg ggtggggag | | | 1560 |
| gtgctggccc ggaacctggc cctccgcttc ggccacatgg accgccttct ggaggcgggc | | | 1620 |
| ctcgaggacc tcctggaggt ggaggggtg gcgagctca ccgcccgggc catcctgaat | | | 1680 |
| accctaaagg acccggagtt ccgggacctg gtgcgccgcc tgaaggaggc cggggtggag | | | 1740 |
| atggaggcca agagcgggga gggcgaggcc ttgaagggc tcaccttcgt catcaccggg | | | 1800 |
| gagcttttccc ggccccggga ggaggtgaag gccctcctta ggcggcttgg ggccaaggtg | | | 1860 |
| acggactcgg tgagccgcaa gacgagcttc tggtggtgg gggagaaccc ggggagcaag | | | 1920 |
| ctggaaaagg cccgcgccct tggggtcccc acctgagcg aggaggagct ctaccgcctc | | | 1980 | attgaggaga ggacgggcaa ggacccaagg gccctcacgg cctag    2025

```
<210> SEQ ID NO 3
<211> LENGTH: 20
<212> TYPE: DNA
<213> ORGANISM: Artificial Sequence
<220> FEATURE:
<223> OTHER INFORMATION: probe or primer
<220> FEATURE:
<221> NAME/KEY: tRNA
<222> LOCATION: (4)..(4)
<223> OTHER INFORMATION: w at position 4 can be T or A
<220> FEATURE:
<221> NAME/KEY: Unsure
<222> LOCATION: (5)..(5)
<223> OTHER INFORMATION: s at position 5 can be C or G
<220> FEATURE:
<221> NAME/KEY: Unsure
<222> LOCATION: (12)..(12)
<223> OTHER INFORMATION: s at position 12 can be C or G
<220> FEATURE:
<221> NAME/KEY: Unsure
<222> LOCATION: (15)..(15)
<223> OTHER INFORMATION: r at position 15 can be G or A
<220> FEATURE:
<221> NAME/KEY: Unsure
<222> LOCATION: (18)..(18)
<223> OTHER INFORMATION: y at position 18 can be T or C

<400> SEQUENCE: 3
atcwscgacg csgartayga    20

<210> SEQ ID NO 4
<211> LENGTH: 7
<212> TYPE: PRT
<213> ORGANISM: Artificial Sequence
<220> FEATURE:
<223> OTHER INFORMATION: protein

<400> SEQUENCE: 4

Ile Ser Asp Ala Glu Tyr Asp
1               5

<210> SEQ ID NO 5
<211> LENGTH: 20
<212> TYPE: DNA
<213> ORGANISM: Artificial Sequence
<220> FEATURE:
<223> OTHER INFORMATION: probe or primer
<220> FEATURE:
<221> NAME/KEY: Unsure
<222> LOCATION: (3)..(3)
<223> OTHER INFORMATION: s at position 3 can be C or G
<220> FEATURE:
<221> NAME/KEY: Unsure
<222> LOCATION: (6)..(6)
<223> OTHER INFORMATION: s at position 6 can be C or G
<220> FEATURE:
<221> NAME/KEY: Unsure
<222> LOCATION: (8)..(8)
<223> OTHER INFORMATION: k at position 8 can be G or T
<220> FEATURE:
<221> NAME/KEY: Unsure
<222> LOCATION: (9)..(9)
<223> OTHER INFORMATION: s at position 9 can be G or C
<220> FEATURE:
<221> NAME/KEY: Unsure
<222> LOCATION: (12)..(12)
<223> OTHER INFORMATION: s at position 12 can be G or C
<220> FEATURE:
<221> NAME/KEY: Unsure
<222> LOCATION: (15)..(15)
<223> OTHER INFORMATION: y at position 15 can be C or T
<220> FEATURE:
<221> NAME/KEY: Unsure
```

```
<222> LOCATION: (18)..(18)
<223> OTHER INFORMATION: r at position 18 can be A or G

<400> SEQUENCE: 5
ccsgtscksc csacytgraa                                           20

<210> SEQ ID NO 6
<211> LENGTH: 20
<212> TYPE: DNA
<213> ORGANISM: Artificial Sequence
<220> FEATURE:
<223> OTHER INFORMATION: probe or primer
<220> FEATURE:
<221> NAME/KEY: Unsure
<222> LOCATION: (9)..(9)
<223> OTHER INFORMATION: v at position 9 can be C, G, or A
<220> FEATURE:
<221> NAME/KEY: Unsure
<222> LOCATION: (11)..(11)
<223> OTHER INFORMATION: r at position 11 can be A or G
<220> FEATURE:
<221> NAME/KEY: Unsure
<222> LOCATION: (12)..(12)
<223> OTHER INFORMATION: y at position 12 can be T or C
<220> FEATURE:
<221> NAME/KEY: Unsure
<222> LOCATION: (16)..(16)
<223> OTHER INFORMATION: s at position 16 is C or G
<220> FEATURE:
<221> NAME/KEY: Unsure
<222> LOCATION: (17)..(17)
<223> OTHER INFORMATION: w at position 17 can be A or T
<220> FEATURE:
<221> NAME/KEY: Unsure
<222> LOCATION: (18)..(18)
<223> OTHER INFORMATION: s at position 18 can be G or C

<400> SEQUENCE: 6
gccttctcva ryttgswscc                                           20

<210> SEQ ID NO 7
<211> LENGTH: 7
<212> TYPE: PRT
<213> ORGANISM: Artificial Sequence
<220> FEATURE:
<223> OTHER INFORMATION: probe or primer

<400> SEQUENCE: 7

Phe Gln Val Gly Arg Thr Gly
1               5

<210> SEQ ID NO 8
<211> LENGTH: 7
<212> TYPE: PRT
<213> ORGANISM: Artificial Sequence
<220> FEATURE:
<223> OTHER INFORMATION: probe or primer

<400> SEQUENCE: 8

Gly Ser Lys Leu Glu Lys Ala
1               5

<210> SEQ ID NO 9
<211> LENGTH: 30
<212> TYPE: DNA
<213> ORGANISM: Artificial Sequence
<220> FEATURE:
<223> OTHER INFORMATION: probe or primer

<400> SEQUENCE: 9
gcgatttcat atgaccctag aggaggcccg                                30
```

-continued

<210> SEQ ID NO 10
<211> LENGTH: 29
<212> TYPE: DNA
<213> ORGANISM: Artificial Sequence
<220> FEATURE:
<223> OTHER INFORMATION: probe or primer

<400> SEQUENCE: 10
gcgggatccg aggccttgga gaagctctt                                    29

<210> SEQ ID NO 11
<211> LENGTH: 33
<212> TYPE: DNA
<213> ORGANISM: Artificial Sequence
<220> FEATURE:
<223> OTHER INFORMATION: probe or primer

<400> SEQUENCE: 11
aaaaccctgt tccagcgtct gcggtgttgc gtc                               33

<210> SEQ ID NO 12
<211> LENGTH: 30
<212> TYPE: DNA
<213> ORGANISM: Artificial Sequence
<220> FEATURE:
<223> OTHER INFORMATION: probe or primer

<400> SEQUENCE: 12
agttgtcata gtttgatcct ctagtctggg                                   30

<210> SEQ ID NO 13
<211> LENGTH: 29
<212> TYPE: DNA
<213> ORGANISM: Artificial Sequence
<220> FEATURE:
<223> OTHER INFORMATION: probe or primer

<400> SEQUENCE: 13
ccctgttcca gcgtctgcgg tgttgcgtt                                    29

<210> SEQ ID NO 14
<211> LENGTH: 59
<212> TYPE: DNA
<213> ORGANISM: Artificial Sequence
<220> FEATURE:
<223> OTHER INFORMATION: probe or primer

<400> SEQUENCE: 14
gggacaaggt cgcagacgcc acaacgcagt caacagtatc aaactaggag atcagaccc   59

<210> SEQ ID NO 15
<211> LENGTH: 184
<212> TYPE: PRT
<213> ORGANISM: Thermus aquaticus
<220> FEATURE:
<221> NAME/KEY: misc_feature
<222> LOCATION: (18)..(120)
<223> OTHER INFORMATION: Xaa can be any naturally occurring amino acid
<220> FEATURE:
<221> NAME/KEY: misc_feature
<222> LOCATION: (126)..(172)
<223> OTHER INFORMATION: Xaa can be any naturally occurring amino acid

<400> SEQUENCE: 15

Tyr Thr Val Glu His Lys Val Asp Gly Leu Ser Val Asn Leu Tyr Tyr
1               5                   10                  15

```
Glu Xaa Xaa Xaa Xaa Xaa Xaa Xaa Xaa Xaa Xaa Xaa Xaa Xaa
         20                  25                  30

Xaa Xaa Xaa Xaa Xaa Xaa Xaa Xaa Xaa Xaa Xaa Xaa Xaa Xaa
             35                  40                  45

Xaa Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa
                 85                  90                  95

Xaa Xaa Xaa Xaa Xaa Xaa Xaa Xaa Xaa Xaa Xaa Xaa Xaa Xaa
                100                 105                 110

Xaa Xaa Xaa Xaa Xaa Xaa Xaa Leu Glu Glu Thr Gly Xaa Xaa Xaa
            115                 120                 125

Xaa Xaa Xaa Xaa Xaa Xaa Xaa Xaa Xaa Xaa Xaa Xaa Xaa Xaa
        130                 135                 140

Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Pro Phe Glu Ala
            165                 170                 175

Asp Gly Val Val Val Lys Leu Asp
            180

<210> SEQ ID NO 16
<211> LENGTH: 187
<212> TYPE: PRT
<213> ORGANISM: Thermus flavus
<220> FEATURE:
<221> NAME/KEY: misc_feature
<222> LOCATION: (18)..(120)
<223> OTHER INFORMATION: Xaa can be any naturally occurring amino acid
<220> FEATURE:
<221> NAME/KEY: misc_feature
<222> LOCATION: (129)..(175)
<223> OTHER INFORMATION: Xaa can be any naturally occurring amino acid

<400> SEQUENCE: 16

Tyr Thr Val Glu His Lys Val Asp Gly Leu Ser Val Asn Leu Tyr Tyr
1               5                  10                  15

Glu Xaa Xaa Xaa Xaa Xaa Xaa Xaa Xaa Xaa Xaa Xaa Xaa Xaa
         20                  25                  30

Xaa Xaa Xaa Xaa Xaa Xaa Xaa Xaa Xaa Xaa Xaa Xaa Xaa Xaa
             35                  40                  45

Xaa Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa
                 85                  90                  95

Xaa Xaa Xaa Xaa Xaa Xaa Xaa Xaa Xaa Xaa Xaa Xaa Xaa Xaa
                100                 105                 110

Xaa Xaa Xaa Xaa Xaa Xaa Xaa Leu Glu Glu Val Glu Arg Glu Gly
            115                 120                 125

Xaa Xaa Xaa Xaa Xaa Xaa Xaa Xaa Xaa Xaa Xaa Xaa Xaa Xaa
        130                 135                 140

Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Pro
```

```
                    165                 170                 175

Phe Glu Ala Asp Gly Val Val Lys Leu Asp
            180                 185

<210> SEQ ID NO 17
<211> LENGTH: 184
<212> TYPE: PRT
<213> ORGANISM: Thermus filiformis
<220> FEATURE:
<221> NAME/KEY: misc_feature
<222> LOCATION: (18)..(120)
<223> OTHER INFORMATION: Xaa can be any naturally occurring amino acid
<220> FEATURE:
<221> NAME/KEY: misc_feature
<222> LOCATION: (126)..(172)
<223> OTHER INFORMATION: Xaa can be any naturally occurring amino acid

<400> SEQUENCE: 17

Tyr Thr Val Glu His Lys Val Asp Gly Leu Ser Val Asn Leu Tyr Tyr
1               5                   10                  15

Glu Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Leu Glu Glu Ser Gly Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Pro Phe Glu Ala
                165                 170                 175

Asp Gly Val Val Val Lys Met Asp
            180

<210> SEQ ID NO 18
<211> LENGTH: 184
<212> TYPE: PRT
<213> ORGANISM: Thermus filiformis
<220> FEATURE:
<221> NAME/KEY: misc_feature
<222> LOCATION: (18)..(120)
<223> OTHER INFORMATION: Xaa can be any naturally occurring amino acid
<220> FEATURE:
<221> NAME/KEY: misc_feature
<222> LOCATION: (126)..(172)
<223> OTHER INFORMATION: Xaa can be any naturally occurring amino acid

<400> SEQUENCE: 18

Tyr Thr Val Glu His Lys Val Asp Gly Leu Ser Val Asn Leu Tyr Tyr
1               5                   10                  15

Glu Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
```

```
                35                  40                  45
Xaa Xaa Xaa Xaa Xaa Xaa Xaa Xaa Xaa Xaa Xaa Xaa Xaa Xaa Xaa
         50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
             100                 105                 110

Xaa Xaa Xaa Xaa Xaa Xaa Xaa Xaa Leu Glu Glu Ser Gly Xaa Xaa Xaa
         115                 120                 125

Xaa Xaa Xaa Xaa Xaa Xaa Xaa Xaa Xaa Xaa Xaa Xaa Xaa Xaa Xaa
         130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Pro Phe Glu Ala
             165                 170                 175

Asp Gly Val Val Val Lys Leu Asp
             180

<210> SEQ ID NO 19
<211> LENGTH: 184
<212> TYPE: PRT
<213> ORGANISM: Thermus sp.
<220> FEATURE:
<221> NAME/KEY: misc_feature
<222> LOCATION: (18)..(120)
<223> OTHER INFORMATION: Xaa can be any naturally occurring amino acid
<220> FEATURE:
<221> NAME/KEY: misc_feature
<222> LOCATION: (126)..(172)
<223> OTHER INFORMATION: Xaa can be any naturally occurring amino acid

<400> SEQUENCE: 19

Tyr Thr Val Glu His Lys Val Asp Gly Leu Ser Val Asn Leu Tyr Tyr
1               5                  10                  15

Glu Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Xaa Xaa Xaa
         50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
             100                 105                 110

Xaa Xaa Xaa Xaa Xaa Xaa Xaa Xaa Leu Glu Glu Ser Gly Xaa Xaa Xaa
         115                 120                 125

Xaa Xaa Xaa Xaa Xaa Xaa Xaa Xaa Xaa Xaa Xaa Xaa Xaa Xaa Xaa
         130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Pro Phe Glu Ala
             165                 170                 175

Asp Gly Val Val Val Lys Leu Asp
             180
```

```
<210> SEQ ID NO 20
<211> LENGTH: 184
<212> TYPE: PRT
<213> ORGANISM: Thermus sp.
<220> FEATURE:
<221> NAME/KEY: misc_feature
<222> LOCATION: (18)..(120)
<223> OTHER INFORMATION: Xaa can be any naturally occurring amino acid
<220> FEATURE:
<221> NAME/KEY: misc_feature
<222> LOCATION: (126)..(172)
<223> OTHER INFORMATION: Xaa can be any naturally occurring amino acid

<400> SEQUENCE: 20

Tyr Thr Val Glu His Lys Val Asp Gly Leu Ser Val Asn Leu Tyr Tyr
1               5                   10                  15

Glu Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
                100                 105                 110

Xaa Xaa Xaa Xaa Xaa Xaa Xaa Xaa Leu Glu Glu Ser Gly Xaa Xaa Xaa
            115                 120                 125

Xaa Xaa Xaa Xaa Xaa Xaa Xaa Xaa Xaa Xaa Xaa Xaa Xaa Xaa Xaa Xaa
130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Pro Phe Glu Ala
                165                 170                 175

Asp Gly Val Val Val Lys Leu Asp
            180

<210> SEQ ID NO 21
<211> LENGTH: 184
<212> TYPE: PRT
<213> ORGANISM: Thermus sp.
<220> FEATURE:
<221> NAME/KEY: misc_feature
<222> LOCATION: (18)..(120)
<223> OTHER INFORMATION: Xaa can be any naturally occurring amino acid
<220> FEATURE:
<221> NAME/KEY: misc_feature
<222> LOCATION: (126)..(172)
<223> OTHER INFORMATION: Xaa can be any naturally occurring amino acid

<400> SEQUENCE: 21

Tyr Thr Val Glu His Lys Val Asp Gly Leu Ser Val Asn Leu Tyr Tyr
1               5                   10                  15

Glu Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa Xaa
50                  55                  60
```

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Leu Glu Glu Ser Gly Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Pro Phe Glu Ala
                165                 170                 175

Asp Gly Val Val Val Lys Leu Asp
            180

<210> SEQ ID NO 22
<211> LENGTH: 184
<212> TYPE: PRT
<213> ORGANISM: Thermus aquaticus
<220> FEATURE:
<221> NAME/KEY: misc_feature
<222> LOCATION: (18)..(120)
<223> OTHER INFORMATION: Xaa can be any naturally occurring amino acid
<220> FEATURE:
<221> NAME/KEY: misc_feature
<222> LOCATION: (126)..(172)
<223> OTHER INFORMATION: Xaa can be any naturally occurring amino acid

<400> SEQUENCE: 22

Tyr Thr Val Glu Arg Lys Val Asp Gly Leu Ser Val Asn Leu Tyr Tyr
1               5                   10                  15

Glu Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Leu Glu Glu Thr Gly Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Pro Phe Glu Ala
                165                 170                 175

Asp Gly Val Val Val Lys Leu Asp
            180

<210> SEQ ID NO 23
<211> LENGTH: 187

```
<212> TYPE: PRT
<213> ORGANISM: Thermus flavus
<220> FEATURE:
<221> NAME/KEY: misc_feature
<222> LOCATION: (18)..(120)
<223> OTHER INFORMATION: Xaa can be any naturally occurring amino acid
<220> FEATURE:
<221> NAME/KEY: misc_feature
<222> LOCATION: (129)..(175)
<223> OTHER INFORMATION: Xaa can be any naturally occurring amino acid

<400> SEQUENCE: 23

Tyr Thr Val Glu His Lys Val Asp Gly Leu Ser Val Asn Leu Tyr Tyr
1               5                   10                  15

Glu Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Leu Glu Glu Val Glu Arg Glu Gly
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Pro
                165                 170                 175

Phe Glu Ala Asp Gly Val Val Val Lys Leu Asp
            180                 185

<210> SEQ ID NO 24
<211> LENGTH: 4
<212> TYPE: PRT
<213> ORGANISM: Artificial Sequence
<220> FEATURE:
<223> OTHER INFORMATION: peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 24

Lys Xaa Asp Gly
1

<210> SEQ ID NO 25
<211> LENGTH: 527
<212> TYPE: PRT
<213> ORGANISM: Thermus aquaticus

<400> SEQUENCE: 25

Pro Glu Leu Lys Ser Pro Asp Ser Pro Thr Glu Gln Val Gly Ala Arg
1               5                   10                  15

Pro Leu Glu Ser Thr Phe Arg Pro Val Arg His Pro Thr Arg Met Tyr
            20                  25                  30
```

```
Ser Leu Asp Asn Ala Phe Ser Leu Asp Glu Val Arg Ala Phe Glu Glu
         35                  40                  45

Arg Ile Glu Arg Ala Leu Gly Arg Lys Gly Pro Phe Leu Tyr Thr Val
 50                  55                  60

Glu His Lys Val Asp Gly Leu Ser Val Asn Leu Tyr Tyr Glu Glu Gly
 65                  70                  75                  80

Ile Leu Val Phe Gly Ala Thr Arg Gly Asp Gly Glu Thr Gly Glu Glu
                 85                  90                  95

Val Thr Gln Asn Leu Leu Thr Ile Arg Thr Ile Pro Arg Arg Leu Thr
                100                 105                 110

Gly Val Pro Asp Arg Leu Glu Val Arg Gly Glu Val Tyr Met Pro Ile
            115                 120                 125

Glu Ala Phe Leu Arg Leu Asn Gln Glu Leu Glu Glu Ala Gly Glu Arg
        130                 135                 140

Ile Phe Lys Asn Pro Arg Asn Ala Ala Ala Gly Ser Leu Arg Gln Lys
145                 150                 155                 160

Asp Pro Arg Val Thr Ala Arg Arg Gly Leu Arg Ala Thr Phe Tyr Ala
                165                 170                 175

Leu Gly Leu Gly Leu Glu Glu Thr Gly Leu Lys Ser Gln His Asp Leu
            180                 185                 190

Leu Leu Trp Leu Lys Glu Arg Gly Phe Pro Val Glu His Gly Phe Thr
        195                 200                 205

Arg Ala Leu Gly Ala Glu Gly Val Glu Glu Val Tyr Gln Ala Trp Leu
    210                 215                 220

Lys Glu Arg Arg Lys Leu Pro Phe Glu Ala Asp Gly Val Val Val Lys
225                 230                 235                 240

Leu Asp Asp Leu Ala Leu Trp Arg Glu Leu Gly Tyr Thr Ala Arg Ala
                245                 250                 255

Pro Arg Phe Ala Leu Ala Tyr Lys Phe Pro Ala Glu Glu Lys Glu Thr
                260                 265                 270

Arg Leu Leu Ser Val Ala Phe Gln Val Gly Arg Thr Gly Arg Ile Thr
        275                 280                 285

Pro Val Gly Val Leu Glu Pro Val Phe Ile Glu Gly Ser Glu Val Ser
    290                 295                 300

Arg Val Thr Leu His Asn Glu Ser Phe Ile Glu Glu Leu Asp Val Arg
305                 310                 315                 320

Ile Gly Asp Trp Val Leu Val His Lys Ala Gly Gly Val Ile Pro Glu
                325                 330                 335

Val Leu Arg Val Leu Lys Glu Arg Thr Gly Glu Glu Lys Pro Ile
                340                 345                 350

Leu Trp Pro Glu Asn Cys Pro Glu Cys Gly His Ala Leu Leu Lys Glu
            355                 360                 365

Gly Lys Val His Arg Cys Pro Asn Pro Leu Cys Pro Ala Lys Arg Phe
    370                 375                 380

Glu Ala Ile Arg His Tyr Ala Ser Arg Lys Ala Met Asp Ile Gln Gly
385                 390                 395                 400

Leu Gly Glu Lys Leu Ile Glu Lys Leu Leu Glu Lys Gly Leu Val Arg
                405                 410                 415

Asp Val Ala Asp Leu Tyr Arg Leu Arg Lys Glu Asp Leu Leu Asp Leu
            420                 425                 430

Glu Arg Met Gly Glu Lys Ser Ala Glu Asn Leu Leu Arg Gln Ile Glu
        435                 440                 445

Glu Ser Lys Gly Arg Gly Leu Glu Arg Leu Leu Tyr Ala Leu Gly Leu
450                 455                 460
```

Pro Gly Val Gly Glu Val Leu Ala Arg Asn Leu Ala Leu Arg Phe Gly
465                 470                 475                 480

His Met Asp Arg Leu Leu Glu Ala Gly Leu Gly Asp Leu Leu Glu Val
                485                 490                 495

Glu Gly Val Gly Glu Leu Thr Ala Arg Ala Ile Leu Asn Thr Leu Lys
            500                 505                 510

Asp Pro Glu Phe Arg Asp Leu Val Arg Arg Leu Lys Glu Ala Gly
        515                 520                 525

<210> SEQ ID NO 26
<211> LENGTH: 557
<212> TYPE: PRT
<213> ORGANISM: Thermus aquaticus

<400> SEQUENCE: 26

Arg Phe Pro Glu Leu Lys Ser Pro Asp Ser Pro Thr Glu Gln Val Gly
1               5                   10                  15

Ala Arg Pro Leu Glu Ala Thr Phe Arg Pro Val Arg His Pro Thr Arg
                20                  25                  30

Met Tyr Ser Leu Asp Asn Ala Phe Asn Phe Asp Glu Leu Lys Ala Phe
            35                  40                  45

Glu Glu Arg Ile Glu Arg Ala Leu Gly Arg Glu Gly Pro Phe Ala Tyr
        50                  55                  60

Thr Val Glu His Lys Val Asp Gly Leu Ser Val Asn Leu Tyr Tyr Glu
65                  70                  75                  80

Asp Gly Val Leu Val Tyr Gly Ala Thr Arg Gly Asp Gly Glu Val Gly
                85                  90                  95

Glu Glu Val Thr Gln Asn Leu Leu Thr Ile Pro Thr Ile Pro Arg Arg
            100                 105                 110

Leu Lys Gly Val Pro Glu Arg Leu Glu Val Arg Gly Glu Val Tyr Met
        115                 120                 125

Pro Val Glu Ala Phe Leu Arg Leu Asn Glu Glu Leu Glu Glu Arg Gly
    130                 135                 140

Ala Arg Ile Phe Lys Asn Pro Arg Asn Ala Ala Ala Gly Ser Leu Arg
145                 150                 155                 160

Gln Lys Asp Pro Arg Ile Thr Ala Lys Arg Gly Leu Arg Ala Thr Phe
                165                 170                 175

Tyr Ala Leu Gly Leu Gly Leu Glu Glu Val Glu Arg Glu Gly Val Ala
            180                 185                 190

Thr Gln Phe Ala Leu Leu His Trp Leu Lys Glu Lys Ser Phe Pro Val
        195                 200                 205

Glu His Gly Tyr Ala Arg Ala Val Gly Ala Glu Gly Val Glu Ala Val
    210                 215                 220

Tyr Gln Asp Trp Leu Lys Lys Arg Arg Ala Leu Pro Phe Glu Ala Asp
225                 230                 235                 240

Gly Val Val Val Lys Leu Asp Glu Leu Ala Leu Trp Arg Glu Leu Gly
                245                 250                 255

Tyr Thr Ala Arg Ala Pro Arg Phe Ala Ile Ala Tyr Lys Phe Pro Ala
            260                 265                 270

Glu Glu Lys Glu Thr Arg Leu Leu Asp Val Ala Phe Gln Val Gly Arg
        275                 280                 285

Thr Gly Arg Val Thr Pro Val Gly Ile Leu Glu Pro Val Phe Leu Glu
    290                 295                 300

Gly Ser Glu Val Ser Arg Val Thr Leu His Asn Glu Ser Tyr Ile Glu
305                 310                 315                 320

```
Glu Leu Asp Ile Arg Ile Gly Asp Trp Val Leu Val His Lys Ala Gly
                325                 330                 335

Gly Val Ile Pro Glu Val Leu Arg Val Leu Lys Glu Arg Thr Gly
            340                 345                 350

Glu Glu Arg Pro Ile Arg Trp Pro Glu Thr Cys Pro Glu Cys Gly His
            355                 360                 365

Arg Leu Leu Lys Glu Gly Lys Val His Arg Cys Pro Asn Pro Leu Cys
        370                 375                 380

Pro Ala Lys Arg Phe Glu Ala Ile Arg His Phe Pro Ser Arg Lys Ala
385                 390                 395                 400

Met Asp Ile Gln Gly Leu Gly Glu Lys Leu Ile Glu Arg Leu Leu Glu
                405                 410                 415

Lys Gly Leu Val Lys Asp Val Ala Asp Leu Tyr Arg Leu Arg Lys Glu
            420                 425                 430

Asp Leu Val Gly Leu Glu Arg Met Gly Glu Lys Ser Ala Gln Asn Leu
        435                 440                 445

Leu Arg Gln Ile Glu Glu Ser Lys Arg Arg Gly Leu Glu Arg Leu Leu
    450                 455                 460

Tyr Ala Leu Gly Leu Pro Gly Val Gly Glu Val Leu Ala Arg Asn Leu
465                 470                 475                 480

Ala Ala Arg Phe Gly Asn Met Asp Arg Leu Leu Glu Ala Ser Leu Glu
                485                 490                 495

Glu Leu Leu Glu Val Glu Glu Val Gly Glu Leu Thr Ala Arg Ala Ile
            500                 505                 510

Leu Glu Thr Leu Lys Asp Pro Ala Phe Arg Asp Leu Val Arg Arg Leu
        515                 520                 525

Lys Glu Ala Gly Val Glu Met Glu Ala Lys Glu Lys Gly Gly Glu Ala
    530                 535                 540

Leu Lys Gly Leu Thr Phe Val Ile Thr Gly Glu Leu Ser
545                 550                 555

<210> SEQ ID NO 27
<211> LENGTH: 546
<212> TYPE: PRT
<213> ORGANISM: Thermus filiformis
<220> FEATURE:
<221> NAME/KEY: misc_feature
<222> LOCATION: (85)..(96)
<223> OTHER INFORMATION: Xaa can be any naturally occurring amino acid
<220> FEATURE:
<221> NAME/KEY: misc_feature
<222> LOCATION: (217)..(219)
<223> OTHER INFORMATION: Xaa can be any naturally occurring amino acid

<400> SEQUENCE: 27

Asp Ser Pro Thr Glu Gln Val Gly Ala Arg Pro Leu Glu Pro Thr Phe
1               5                   10                  15

Arg Pro Val Arg His Pro Thr Arg Met Tyr Ser Leu Asp Asn Ala Phe
                20                  25                  30

Thr Tyr Glu Glu Val Leu Ala Phe Glu Glu Arg Leu Asp Arg Ala Leu
            35                  40                  45

Gly Arg Lys Arg Pro Phe Leu Tyr Thr Val Glu His Lys Val Asp Gly
        50                  55                  60

Leu Ser Val Asn Leu Tyr Tyr Glu Glu Gly Val Leu Val Phe Gly Ala
65                  70                  75                  80

Thr Arg Gly Asp Xaa Xaa Xaa Xaa Xaa Xaa Xaa Xaa Xaa Xaa Xaa Xaa
                85                  90                  95
```

-continued

```
Thr Ile Pro Thr Ile Pro Arg Arg Leu Lys Gly Val Pro Asp Arg Leu
            100                 105                 110

Glu Val Arg Gly Glu Val Tyr Met Pro Ile Glu Ala Phe Leu Arg Leu
        115                 120                 125

Asn Glu Glu Leu Glu Glu Arg Gly Glu Lys Val Phe Lys Asn Pro Arg
130                 135                 140

Asn Ala Ala Ala Gly Ser Leu Arg Gln Lys Asp Pro Arg Val Thr Ala
145                 150                 155                 160

Lys Arg Gly Leu Arg Ala Thr Phe Tyr Ala Leu Gly Leu Gly Leu Glu
                165                 170                 175

Glu Ser Gly Leu Lys Ser Gln Tyr Glu Leu Leu Trp Leu Lys Glu
        180                 185                 190

Lys Gly Phe Pro Val Glu His Gly Tyr Glu Lys Ala Leu Gly Ala Glu
            195                 200                 205

Gly Val Glu Glu Val Tyr Gln Ala Xaa Xaa Xaa Lys Arg His Ala Leu
210                 215                 220

Pro Phe Glu Ala Asp Gly Val Val Lys Met Asp Asp Leu Thr Leu
225                 230                 235                 240

Trp Gly Glu Leu Gly Tyr Thr Ala Arg Ala Pro Arg Phe Ala Ile Ala
                245                 250                 255

Tyr Lys Phe Pro Ala Glu Glu Asn Glu Thr Arg Leu Leu Asp Val Asp
            260                 265                 270

Phe Gln Val Gly Arg Thr Gly Arg Val Thr Pro Val Gly Ile Leu Glu
        275                 280                 285

Pro Val Phe Leu Glu Gly Ser Glu Val Ser Arg Val Thr Leu His Asn
    290                 295                 300

Glu Ser Tyr Ile Glu Glu Leu Asp Ile Arg Ile Gly Asp Trp Val Leu
305                 310                 315                 320

Val His Lys Ala Gly Gly Val Ile Pro Glu Val Leu Arg Val Leu Lys
                325                 330                 335

Glu Arg Arg Thr Gly Glu Glu Arg Pro Ile Arg Trp Pro Glu Thr Cys
            340                 345                 350

Pro Glu Cys Gly His Arg Leu Leu Lys Glu Gly Lys Val His Arg Cys
        355                 360                 365

Pro Asn Pro Leu Cys Pro Ala Lys Arg Phe Glu Ala Ile Arg His Phe
370                 375                 380

Pro Ser Arg Lys Ala Met Asp Ile Gln Gly Leu Gly Glu Lys Leu Ile
385                 390                 395                 400

Glu Arg Leu Leu Glu Lys Gly Leu Val Lys Asp Val Ala Asp Leu Tyr
                405                 410                 415

Arg Leu Arg Lys Glu Asp Leu Val Gly Leu Glu Arg Met Gly Glu Lys
            420                 425                 430

Ser Ala Gln Asn Leu Leu Arg Gln Ile Glu Glu Ser Lys Arg Arg Gly
        435                 440                 445

Leu Glu Arg Leu Leu Tyr Ala Leu Gly Leu Pro Gly Val Gly Glu Val
    450                 455                 460

Leu Ala Arg Asn Leu Ala Ala Arg Phe Gly Asn Met Asp Arg Leu Leu
465                 470                 475                 480

Glu Ala Ser Leu Glu Glu Leu Leu Glu Val Glu Glu Val Gly Glu Leu
                485                 490                 495

Thr Ala Arg Ala Ile Leu Glu Thr Leu Lys Asp Pro Ala Phe Arg Asp
            500                 505                 510

Leu Val Arg Arg Leu Lys Glu Ala Gly Val Glu Met Glu Ala Lys Glu
        515                 520                 525
```

Lys Gly Gly Glu Ala Leu Lys Gly Leu Thr Phe Val Ile Thr Gly Glu
        530                 535                 540

Leu Ser
545

<210> SEQ ID NO 28
<211> LENGTH: 537
<212> TYPE: PRT
<213> ORGANISM: Thermus filiformis

<400> SEQUENCE: 28

Arg Phe Pro Glu Phe Lys Ser Pro Asp Ser Pro Thr Glu Gln Val Gly
1               5                   10                  15

Ala Arg Pro Leu Glu Pro Thr Phe Arg Pro Val Arg His Pro Thr Arg
            20                  25                  30

Met Tyr Ser Leu Asp Asn Ala Phe Thr Tyr Glu Glu Val Leu Ala Phe
        35                  40                  45

Glu Glu Arg Leu Glu Arg Ala Leu Gly Arg Lys Arg Pro Phe Leu Tyr
    50                  55                  60

Thr Val Glu His Lys Val Asp Gly Leu Ser Val Asn Leu Tyr Tyr Glu
65                  70                  75                  80

Glu Gly Val Leu Val Phe Gly Ala Thr Arg Gly Asp Gly Glu Val Gly
                85                  90                  95

Glu Glu Val Thr Gln Asn Leu Leu Thr Ile Pro Thr Ile Pro Arg Arg
            100                 105                 110

Leu Lys Gly Val Pro Asp Arg Leu Glu Val Arg Gly Glu Val Tyr Met
        115                 120                 125

Pro Ile Glu Ala Phe Leu Arg Leu Asn Glu Glu Leu Glu Glu Arg Gly
    130                 135                 140

Glu Lys Val Phe Lys Asn Pro Arg Asn Ala Ala Ala Gly Ser Leu Arg
145                 150                 155                 160

Gln Lys Asp Pro Arg Val Thr Ala Lys Arg Gly Leu Arg Ala Thr Phe
                165                 170                 175

Tyr Ala Leu Gly Leu Gly Leu Glu Glu Ser Gly Leu Lys Ser Gln Tyr
            180                 185                 190

Glu Leu Leu Leu Trp Leu Lys Glu Lys Gly Phe Pro Val Glu His Gly
        195                 200                 205

Tyr Glu Lys Ala Leu Gly Ala Glu Gly Val Glu Glu Val Tyr Arg Arg
    210                 215                 220

Phe Leu Ala Gln Arg His Ala Leu Pro Phe Glu Ala Asp Gly Val Val
225                 230                 235                 240

Val Lys Leu Asp Asp Leu Ala Leu Trp Arg Glu Leu Gly Tyr Thr Ala
                245                 250                 255

Arg Ala Pro Arg Phe Ala Leu Ala Tyr Lys Phe Pro Ala Glu Glu Lys
            260                 265                 270

Glu Thr Arg Leu Leu Asp Val Val Phe Gln Val Gly Arg Thr Gly Arg
        275                 280                 285

Val Thr Pro Val Gly Val Leu Glu Pro Val Phe Ile Glu Gly Ser Glu
    290                 295                 300

Val Ser Arg Val Thr Leu His Asn Glu Ser Tyr Ile Glu Glu Leu Asp
305                 310                 315                 320

Ile Arg Ile Gly Asp Trp Val Leu Val His Lys Ala Gly Gly Val Ile
                325                 330                 335

Pro Glu Val Leu Arg Val Leu Lys Glu Arg Arg Thr Gly Glu Glu Arg
            340                 345                 350

```
Pro Ile Arg Trp Pro Glu Thr Cys Pro Glu Cys Gly His Arg Leu Val
            355                 360                 365
Lys Glu Gly Lys Val His Arg Cys Pro Asn Pro Leu Cys Pro Ala Lys
        370                 375                 380
Arg Phe Glu Ala Ile Arg His Tyr Ala Ser Arg Lys Ala Met Asp Ile
385                 390                 395                 400
Glu Gly Leu Gly Glu Lys Leu Ile Glu Arg Leu Leu Glu Lys Gly Leu
                405                 410                 415
Val Arg Asp Val Ala Asp Leu Tyr His Leu Arg Lys Glu Asp Leu Leu
            420                 425                 430
Gly Leu Glu Arg Met Gly Glu Lys Ser Ala Gln Asn Leu Leu Arg Gln
        435                 440                 445
Ile Glu Glu Ser Lys His Arg Gly Leu Glu Arg Leu Leu Tyr Ala Leu
    450                 455                 460
Gly Leu Pro Gly Val Gly Glu Val Leu Ala Arg Asn Leu Ala Arg Arg
465                 470                 475                 480
Phe Gly Thr Met Asp Arg Leu Leu Glu Ala Ser Leu Glu Glu Leu Leu
                485                 490                 495
Glu Val Glu Glu Val Gly Glu Leu Thr Ala Arg Ala Ile Leu Glu Thr
            500                 505                 510
Leu Lys Asp Pro Ala Phe Arg Asp Leu Val Arg Arg Leu Lys Glu Ala
        515                 520                 525
Gly Val Ser Met Glu Ser Lys Glu Glu
    530                 535

<210> SEQ ID NO 29
<211> LENGTH: 505
<212> TYPE: PRT
<213> ORGANISM: Thermus sp.

<400> SEQUENCE: 29

Pro Ser Pro Asp Ser Pro Thr Glu Gln Val Gly Ala Lys Pro Leu Glu
1               5                   10                  15
Ala Thr Phe Arg Pro Ile Arg His Pro Thr Arg Met Tyr Ser Leu Asp
            20                  25                  30
Asn Ala Phe Thr Leu Glu Glu Val Arg Thr Phe Glu Glu Arg Ile Glu
        35                  40                  45
Arg Ala Leu Gly Arg Lys Gly Pro Phe Val Tyr Thr Val Glu His Lys
    50                  55                  60
Val Asp Gly Leu Ser Val Asn Leu Tyr Tyr Glu Gly Ile Leu Val
65                  70                  75              80
Trp Gly Ala Thr Arg Gly Asp Gly Glu Thr Gly Glu Glu Val Thr Gln
                85                  90                  95
Asn Leu Leu Thr Ile Pro Thr Ile Pro Arg Arg Leu Lys Gly Val Pro
            100                 105                 110
Glu Arg Leu Glu Val Arg Gly Glu Val Tyr Met Pro Ile Glu Ala Phe
        115                 120                 125
Leu Arg Leu Asn Glu Glu Leu Glu Glu Lys Gly Glu Lys Ile Phe Lys
    130                 135                 140
Asn Pro Arg Asn Ala Ala Ala Gly Ser Phe Arg Gln Lys Asp Pro Arg
145                 150                 155                 160
Ile Thr Ala Arg Arg Gly Leu Arg Ala Thr Phe Tyr Ala Leu Gly Leu
                165                 170                 175
Gly Leu Glu Glu Ser Gly Leu Lys Thr Gln Leu Asp Leu Leu His Trp
            180                 185                 190
```

```
Leu Arg Glu Lys Gly Phe Pro Val Glu His Gly Phe Ala Arg Ala Glu
            195                 200                 205

Gly Ala Glu Gly Val Glu Arg Ile Tyr Gln Gly Trp Leu Lys Glu Arg
            210                 215                 220

Arg Ser Leu Pro Phe Glu Ala Asp Gly Val Val Lys Leu Asp Glu
225                 230                 235                 240

Leu Ser Leu Trp Arg Glu Leu Gly Tyr Thr Ala Arg Ala Pro Arg Phe
            245                 250                 255

Ala Ile Ala Tyr Lys Phe Pro Ala Glu Glu Lys Glu Thr Ala Leu Phe
            260                 265                 270

Gln Val Val Leu Gln Val Gly Arg Thr Gly Gln Val Thr Pro Val Gly
            275                 280                 285

Ile Leu Glu Pro Val Phe Ile Glu Gly Ser Val Ser Arg Val Thr
            290                 295                 300

Leu His Asn Glu Ser Tyr Ile Glu Asp Leu Asp Val Arg Ile Gly Glu
305                 310                 315                 320

Trp Val Leu Val His Asn Ala Gly Gly Val Ile Pro Glu Val Leu Arg
            325                 330                 335

Val Leu Lys Glu Lys Arg Thr Gly Glu Glu Arg Pro Ile Arg Trp Pro
            340                 345                 350

Glu Thr Cys Pro Glu Cys Gly His Arg Leu Val Lys Glu Gly Lys Val
            355                 360                 365

His Arg Cys Pro Asn Pro Leu Cys Pro Ala Lys Arg Phe Glu Ala Ile
            370                 375                 380

Arg His Tyr Ala Ser Arg Lys Ala Met Asp Ile Gly Gly Leu Gly Glu
385                 390                 395                 400

Lys Leu Ile Glu Lys Leu Leu Glu Lys Gly Leu Val Lys Asp Val Ala
            405                 410                 415

Asp Leu Tyr Arg Leu Lys Glu Glu Asp Leu Val Gly Leu Glu Arg Met
            420                 425                 430

Gly Lys Lys Ser Ala Gln Asn Leu Leu Arg Gln Ile Glu Lys Ser Lys
            435                 440                 445

Ala Arg Gly Leu Glu Arg Leu Leu Tyr Ala Leu Gly Leu Pro Gly Val
            450                 455                 460

Gly Glu Val Leu Ala Arg Asn Leu Ala Ala His Phe Gly Thr Met Asp
465                 470                 475                 480

Arg Leu Leu Glu Ala Ser Leu Glu Glu Leu Leu Gln Val Glu Val
            485                 490                 495

Gly Glu Leu Thr Ala Arg Gly Ile Tyr
            500                 505

<210> SEQ ID NO 30
<211> LENGTH: 481
<212> TYPE: PRT
<213> ORGANISM: Thermus sp.

<400> SEQUENCE: 30

Asp Asn Ala Phe Thr His His Asp Leu Lys Ala Phe Glu Asp Arg Val
1               5                   10                  15

Asp Arg Ala Leu Gly Arg Glu Gly Pro Phe Val Tyr Thr Val Glu His
            20                  25                  30

Lys Val Asp Gly Leu Ser Val Asn Leu Tyr Tyr Glu Glu Gly Ile Leu
            35                  40                  45

Val Phe Gly Ala Pro Arg Gly Asp Gly Glu Val Gly Glu Glu Val Thr
50                  55                  60
```

```
Gln Asn Leu Leu Thr Ile Pro Thr Ile Pro Arg Arg Leu Lys Gly Val
 65                  70                  75                  80

Pro Glu Arg Leu Glu Val Arg Gly Glu Val Tyr Met Pro Ile Glu Ala
                 85                  90                  95

Phe Leu Arg Leu Asn Glu Glu Leu Glu Ala Gly Glu Lys Val Phe
                100                 105                 110

Lys Asn Pro Arg Asn Ala Ala Gly Ser Leu Arg Gln Lys Asp Pro
                115                 120                 125

Arg Ile Thr Ala Lys Arg Gly Leu Arg Ala Thr Phe Tyr Ala Leu Gly
                130                 135                 140

Leu Gly Leu Glu Glu Ser Gly Leu Lys Thr Gln Tyr Glu Phe Leu Leu
145                 150                 155                 160

Trp Phe Lys Glu Lys Gly Phe Pro Val Glu His Gly Phe Ala Arg Ala
                165                 170                 175

Thr Gly Ala Glu Gly Val Glu Arg Val Tyr Gln Gly Trp Leu Gln Lys
                180                 185                 190

Arg Arg Lys Leu Pro Phe Glu Ala Asp Gly Val Val Lys Leu Asp
                195                 200                 205

Glu Leu Ala Leu Trp Arg Glu Leu Gly Tyr Thr Ala Arg Ala Pro Arg
210                 215                 220

Phe Ala Ile Ala Tyr Lys Phe Pro Ala Glu Glu Lys Glu Thr Arg Leu
225                 230                 235                 240

Leu Asp Val Val Phe Gln Val Gly Arg Thr Gly Arg Val Thr Pro Val
                245                 250                 255

Gly Ile Leu Glu Pro Val Leu Ile Glu Gly Ser Glu Val Ser Arg Val
                260                 265                 270

Thr Leu His Asn Glu Ser Tyr Ile Glu Glu Leu Asp Ile Arg Ile Gly
                275                 280                 285

Asp Trp Val Leu Val His Lys Ala Gly Gly Val Ile Pro Glu Val Leu
                290                 295                 300

Arg Val Leu Lys Glu Arg Arg Thr Gly Ala Glu Arg Pro Ile Val Trp
305                 310                 315                 320

Pro Glu Asn Cys Pro Glu Cys Gly His His Leu Val Lys Glu Gly Lys
                325                 330                 335

Val His Arg Cys Pro Asn Pro Leu Cys Pro Ala Lys Arg Phe Glu Ala
                340                 345                 350

Ile Arg His Tyr Ala Ser Arg Lys Ala Met Asp Ile Gln Gly Leu Gly
                355                 360                 365

Glu Lys Leu Ile Glu Lys Leu Leu Glu Asn Gly Leu Val Lys Asp Val
                370                 375                 380

Ala Asp Leu Tyr Arg Leu Arg Lys Glu Asp Leu Val Gly Leu Glu Arg
385                 390                 395                 400

Met Gly Glu Lys Ser Ala Glu Asn Leu Leu Arg Gln Ile Glu Glu Ser
                405                 410                 415

Lys His Arg Gly Leu Glu Arg Leu Leu Tyr Ala Leu Gly Leu Pro Gly
                420                 425                 430

Val Gly Glu Val Leu Ala Arg Asn Leu Ala Ala Arg Phe Gly Thr Met
                435                 440                 445

Asp Arg Leu Leu Glu Ala Thr Leu Glu Glu Leu Leu Glu Val Glu Glu
                450                 455                 460

Val Gly Glu Leu Thr Ala Arg Gly Ile Trp Glu Thr Leu Gln Asp Pro
465                 470                 475                 480

Ala
```

<210> SEQ ID NO 31
<211> LENGTH: 674
<212> TYPE: PRT
<213> ORGANISM: Thermus scotoductus

<400> SEQUENCE: 31

| | | | | | | | | | | | | | | |
|---|---|---|---|---|---|---|---|---|---|---|---|---|---|---|
| Met | Thr | Leu | Glu | Glu | Ala | Arg | Lys | Arg | Val | Asn | Glu | Leu | Arg | Asp | Leu |
| 1 | | | | 5 | | | | | 10 | | | | | 15 | |
| Ile | Arg | Tyr | His | Asn | Tyr | Arg | Tyr | Tyr | Val | Leu | Ala | Asp | Pro | Glu | Ile |
| | | | 20 | | | | | 25 | | | | | 30 | | |
| Ser | Asp | Ala | Glu | Tyr | Asp | Arg | Leu | Leu | Arg | Glu | Leu | Lys | Glu | Leu | Glu |
| | | 35 | | | | | 40 | | | | | 45 | | | |
| Glu | Arg | Phe | Pro | Glu | Leu | Lys | Ser | Pro | Asp | Ser | Pro | Thr | Glu | Gln | Val |
| | 50 | | | | | 55 | | | | | 60 | | | | |
| Gly | Ala | Lys | Pro | Leu | Glu | Ala | Thr | Phe | Arg | Pro | Ile | Arg | His | Pro | Thr |
| 65 | | | | | 70 | | | | | 75 | | | | | 80 |
| Arg | Met | Tyr | Ser | Leu | Asp | Asn | Ala | Phe | Asn | Phe | Asp | Glu | Leu | Lys | Ala |
| | | | | 85 | | | | | 90 | | | | | 95 | |
| Phe | Glu | Glu | Arg | Ile | Gly | Arg | Ala | Leu | Gly | Arg | Glu | Gly | Pro | Phe | Ala |
| | | | 100 | | | | | 105 | | | | | 110 | | |
| Tyr | Thr | Val | Glu | His | Lys | Val | Asp | Gly | Leu | Ser | Val | Asn | Leu | Tyr | Tyr |
| | | 115 | | | | | 120 | | | | | 125 | | | |
| Glu | Asp | Gly | Val | Leu | Val | Trp | Gly | Ala | Thr | Arg | Gly | Asp | Gly | Glu | Val |
| | 130 | | | | | 135 | | | | | 140 | | | | |
| Gly | Glu | Glu | Val | Thr | Gln | Asn | Leu | Leu | Thr | Ile | Pro | Thr | Ile | Pro | Arg |
| 145 | | | | | 150 | | | | | 155 | | | | | 160 |
| Arg | Val | Lys | Gly | Val | Pro | Glu | Arg | Leu | Glu | Val | Arg | Gly | Glu | Val | Tyr |
| | | | | 165 | | | | | 170 | | | | | 175 | |
| Met | Pro | Ile | Glu | Ala | Phe | Leu | Arg | Leu | Asn | Glu | Glu | Leu | Glu | Glu | Lys |
| | | | 180 | | | | | 185 | | | | | 190 | | |
| Gly | Glu | Lys | Ile | Phe | Lys | Asn | Pro | Arg | Asn | Ala | Ala | Ala | Gly | Ser | Leu |
| | | 195 | | | | | 200 | | | | | 205 | | | |
| Arg | Gln | Lys | Asp | Pro | Arg | Ile | Thr | Ala | Arg | Arg | Gly | Leu | Arg | Ala | Thr |
| | 210 | | | | | 215 | | | | | 220 | | | | |
| Phe | Tyr | Ala | Leu | Gly | Leu | Gly | Leu | Glu | Glu | Ser | Gly | Leu | Lys | Thr | Gln |
| 225 | | | | | 230 | | | | | 235 | | | | | 240 |
| Leu | Asp | Leu | Leu | His | Trp | Leu | Arg | Glu | Lys | Gly | Phe | Pro | Val | Glu | His |
| | | | | 245 | | | | | 250 | | | | | 255 | |
| Gly | Phe | Ala | Arg | Ala | Glu | Gly | Ala | Glu | Gly | Val | Glu | Arg | Ile | Tyr | Gln |
| | | | 260 | | | | | 265 | | | | | 270 | | |
| Gly | Trp | Leu | Lys | Glu | Arg | Arg | Ser | Leu | Pro | Phe | Glu | Ala | Asp | Gly | Val |
| | | 275 | | | | | 280 | | | | | 285 | | | |
| Val | Val | Lys | Leu | Asp | Glu | Leu | Ser | Leu | Trp | Arg | Glu | Leu | Gly | Tyr | Thr |
| | 290 | | | | | 295 | | | | | 300 | | | | |
| Ala | Arg | Ala | Pro | Arg | Phe | Ala | Ile | Ala | Tyr | Lys | Phe | Pro | Ala | Glu | Glu |
| 305 | | | | | 310 | | | | | 315 | | | | | 320 |
| Lys | Glu | Thr | Arg | Leu | Leu | Gln | Val | Val | Phe | Gln | Val | Gly | Arg | Thr | Gly |
| | | | | 325 | | | | | 330 | | | | | 335 | |
| Arg | Val | Thr | Pro | Val | Gly | Ile | Leu | Glu | Pro | Val | Phe | Ile | Glu | Gly | Ser |
| | | | 340 | | | | | 345 | | | | | 350 | | |
| Val | Val | Ser | Arg | Val | Thr | Leu | His | Asn | Glu | Ser | Tyr | Ile | Glu | Glu | Leu |
| | | 355 | | | | | 360 | | | | | 365 | | | |
| Asp | Val | Arg | Ile | Gly | Asp | Trp | Val | Leu | Val | His | Lys | Ala | Gly | Gly | Val |
| | 370 | | | | | 375 | | | | | 380 | | | | |

```
Ile Pro Glu Val Leu Arg Val Leu Lys Glu Lys Arg Thr Gly Glu Glu
385                 390                 395                 400

Arg Pro Ile Arg Trp Pro Glu Thr Cys Pro Glu Cys Gly His Arg Leu
            405                 410                 415

Val Lys Glu Gly Lys Val His Arg Cys Pro Asn Pro Leu Cys Pro Ala
            420                 425                 430

Lys Arg Phe Glu Ala Ile Arg His Tyr Ala Ser Arg Lys Ala Met Asp
            435                 440                 445

Ile Gly Gly Leu Gly Glu Lys Leu Ile Glu Lys Leu Leu Glu Lys Gly
            450                 455                 460

Leu Val Lys Asp Val Ala Asp Leu Tyr Arg Leu Lys Lys Glu Asp Leu
465                 470                 475                 480

Leu Gly Leu Glu Arg Met Gly Glu Lys Ser Ala Gln Asn Leu Leu Arg
                485                 490                 495

Gln Ile Glu Glu Ser Lys Gly Arg Gly Leu Glu Arg Leu Leu Tyr Ala
                500                 505                 510

Leu Gly Leu Pro Gly Val Gly Glu Val Leu Ala Arg Asn Leu Ala Ala
                515                 520                 525

His Phe Gly Thr Met Asp Arg Leu Leu Glu Ala Ser Leu Glu Glu Leu
                530                 535                 540

Leu Gln Val Glu Val Gly Glu Leu Thr Ala Arg Gly Ile Tyr Glu
545                 550                 555                 560

Thr Leu Gln Asp Pro Ala Phe Arg Asp Leu Val Arg Arg Leu Lys Glu
                565                 570                 575

Ala Gly Val Val Met Glu Ala Lys Glu Arg Gly Glu Glu Ala Leu Lys
                580                 585                 590

Gly Leu Thr Phe Val Ile Thr Gly Glu Leu Ser Arg Pro Arg Glu Glu
                595                 600                 605

Val Lys Ala Leu Leu Arg Arg Leu Gly Ala Lys Val Thr Asp Ser Val
            610                 615                 620

Ser Arg Lys Thr Ser Tyr Leu Val Val Gly Glu Asn Pro Gly Ser Lys
625                 630                 635                 640

Leu Glu Lys Ala Arg Ala Leu Gly Val Pro Thr Leu Thr Glu Glu Glu
                645                 650                 655

Leu Tyr Arg Leu Ile Glu Glu Arg Thr Gly Lys Pro Val Glu Thr Leu
                660                 665                 670

Ala Ser
```